US011248261B2

(12) United States Patent
Fichou et al.

(10) Patent No.: US 11,248,261 B2
(45) Date of Patent: Feb. 15, 2022

(54) RHD GENE ALLELE ASSOCIATED WITH A WEAK D PHENOTYPE AND ITS USES

(71) Applicants: ETABLISSEMENT FRANCAIS DU SANG, La Plaine Saint Denis (FR); INSERM (INSTITUT NATIONAL DE LA SANTE ET DE LA RECHERCHE MEDICALE), Paris (FR); NATIONAL INSTITUTE OF IMMUNOHAEMATOLOGY, Mumbai (IN); UNIVERSITE DE BRETAGNE OCCIDENTALE (UBO), Brest (FR)

(72) Inventors: Yann Fichou, Brest (FR); Swati Kulkarni, Mumbai (IN)

(73) Assignees: ETABLISSEMENT FRANCAIS DU SANG, La Plaine Saint Denis (FR); INSERM (INSTITUT NATIONAL DE LA SANTÉ ET DE LA RECHERCHE MÉDICALE), Paris (FR); NATIONAL INSTITUTE OF IMMUNOHAEMATOLOGY, Mumbai (IN); UNIVERSITE DE BRETAGNE OCCIDENTALE (UBO), Brest (FR)

( * ) Notice: Subject to any disclaimer, the term of this patent is extended or adjusted under 35 U.S.C. 154(b) by 172 days.

(21) Appl. No.: 16/491,645

(22) PCT Filed: Mar. 7, 2018

(86) PCT No.: PCT/EP2018/055529
§ 371 (c)(1),
(2) Date: Sep. 6, 2019

(87) PCT Pub. No.: WO2018/162516
PCT Pub. Date: Sep. 13, 2018

(65) Prior Publication Data
US 2020/0291451 A1    Sep. 17, 2020

(30) Foreign Application Priority Data

Mar. 8, 2017 (EP) ..................... 17305246

(51) Int. Cl.
*C12Q 1/686*    (2018.01)
*C12Q 1/6881*   (2018.01)

(52) U.S. Cl.
CPC .......... *C12Q 1/686* (2013.01); *C12Q 1/6881* (2013.01); *C12Q 2537/143* (2013.01); *C12Q 2600/16* (2013.01); *C12Q 2600/172* (2013.01)

(58) Field of Classification Search
None
See application file for complete search history.

(56) References Cited

FOREIGN PATENT DOCUMENTS

WO   WO-2008151110 A2 * 12/2008 .......... C12Q 1/6886
WO   WO 2012/171990      12/2012

OTHER PUBLICATIONS

Wagner et al. Molecular Basis of Weak D Phenotypes (1999) Blood vol. 93, No. 1 pp. 385-393. (Year: 1999).*

(Continued)

*Primary Examiner* — Jeanine A Goldberg
*Assistant Examiner* — Jennifer L. Overly
(74) *Attorney, Agent, or Firm* — Saliwanchik, Lloyd & Eisenschenk

(57) ABSTRACT

The present invention relates to the identification of a novel allele of the RHD gene associated with a weak D phenotype and the kits and methods for detecting this allele.

10 Claims, 6 Drawing Sheets
Specification includes a Sequence Listing.

(56) References Cited

OTHER PUBLICATIONS

Flegel et al. Molecular Biology of partial D and weak D: Implications for Blood Bank Practice (2002) Clin. Lab. 48:53-59. (Year: 2002).*
Wagner et al. The Rhesus Site (2014) Transf Med Hemother 5:357-363. (Year: 2014).*
Written Opinion in International Application No. PCT/EP2018/055529, dated May 16, 2018, pp. 1-6.

* cited by examiner

SEQUENCE LISTING

<160> NUMBER OF SEQ ID NOS: 41

<210> SEQ ID NO 1
<211> LENGTH: 28
<212> TYPE: DNA
<213> ORGANISM: artificial sequence
<220> FEATURE:
<223> OTHER INFORMATION: primer

<400> SEQUENCE: 1 ataccttga attaagcact tcacagag                               28

<210> SEQ ID NO 2
<211> LENGTH: 22
<212> TYPE: DNA
<213> ORGANISM: artificial sequence
<220> FEATURE:
<223> OTHER INFORMATION: primer

<400> SEQUENCE: 2
actgtgacca cccagcattc ta                                    22

<210> SEQ ID NO 3
<211> LENGTH: 21
<212> TYPE: DNA
<213> ORGANISM: artificial sequence
<220> FEATURE:
<223> OTHER INFORMATION: primer

<400> SEQUENCE: 3
acgtgttgag ggcatgacct c                                     21

<210> SEQ ID NO 4
<211> LENGTH: 23
<212> TYPE: DNA
<213> ORGANISM: artificial sequence
<220> FEATURE:
<223> OTHER INFORMATION: primer

<400> SEQUENCE: 4
gcctggattc cttgtgatac acg                                   23

<210> SEQ ID NO 5
<211> LENGTH: 24
<212> TYPE: DNA
<213> ORGANISM: artificial sequence
<220> FEATURE:
<223> OTHER INFORMATION: primer

<400> SEQUENCE: 5
aggctgtttc aagagatcaa gcca                                  24

<210> SEQ ID NO 6
<211> LENGTH: 25
<212> TYPE: DNA
<213> ORGANISM: artificial sequence
<220> FEATURE:
<223> OTHER INFORMATION: primer

<400> SEQUENCE: 6
gatgttgtta tgtggtacat ggctg                                 25

<210> SEQ ID NO 7
<211> LENGTH: 21
<212> TYPE: DNA
<213> ORGANISM: artificial sequence

```
<220> FEATURE:
<223> OTHER INFORMATION: primer

<400> SEQUENCE: 7
ccccacacac atgcacttac c                                              21

<210> SEQ ID NO 8
<211> LENGTH: 21
<212> TYPE: DNA
<213> ORGANISM: artificial sequence
<220> FEATURE:
<223> OTHER INFORMATION: primer

<400> SEQUENCE: 8
cctagtccca gggctttgat t                                              21

<210> SEQ ID NO 9
<211> LENGTH: 20
<212> TYPE: DNA
<213> ORGANISM: artificial sequence
<220> FEATURE:
<223> OTHER INFORMATION: universal primer sequence

<400> SEQUENCE: 9
gtcgtagtcg acgaccgtta                                                20

<210> SEQ ID NO 10
<211> LENGTH: 22
<212> TYPE: DNA
<213> ORGANISM: artificial sequence
<220> FEATURE:
<223> OTHER INFORMATION: primer

<400> SEQUENCE: 10
agcaggacct tggtctttcc tt                                             22

<210> SEQ ID NO 11
<211> LENGTH: 20
<212> TYPE: DNA
<213> ORGANISM: artificial sequence
<220> FEATURE:
<223> OTHER INFORMATION: primer

<400> SEQUENCE: 11
acccttgctg tggttgtgat                                                20

<210> SEQ ID NO 12
<211> LENGTH: 22
<212> TYPE: DNA
<213> ORGANISM: artificial sequence
<220> FEATURE:
<223> OTHER INFORMATION: primer

<400> SEQUENCE: 12
accatgacat tgcccttctg ga                                             22

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
agacatgtgg ctcggtcaac aa                                             22
```

<210> SEQ ID NO 14
<211> LENGTH: 21
<212> TYPE: DNA
<213> ORGANISM: artificial sequence
<220> FEATURE:
<223> OTHER INFORMATION: primer

<400> SEQUENCE: 14
cttgggcttc ctcacctcga g                                     21

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15
tgtgatgacc accttcccag a                                     21

<210> SEQ ID NO 16
<211> LENGTH: 24
<212> TYPE: DNA
<213> ORGANISM: artificial sequence
<220> FEATURE:
<223> OTHER INFORMATION: primer

<400> SEQUENCE: 16 agcccccta atgctgctaga caat                                  24

<210> SEQ ID NO 17
<211> LENGTH: 26
<212> TYPE: DNA
<213> ORGANISM: artificial sequence
<220> FEATURE:
<223> OTHER INFORMATION: primer

<400> SEQUENCE: 17
ttcttagcat ttcacacaaa tgcatg                                26

<210> SEQ ID NO 18
<211> LENGTH: 24
<212> TYPE: DNA
<213> ORGANISM: artificial sequence
<220> FEATURE:
<223> OTHER INFORMATION: primer

<400> SEQUENCE: 18
cactgtgtcc agcctaaaac tgtt                                  24

<210> SEQ ID NO 19
<211> LENGTH: 22
<212> TYPE: DNA
<213> ORGANISM: artificial sequence
<220> FEATURE:
<223> OTHER INFORMATION: primer

<400> SEQUENCE: 19
gatcacctga acccagtgag gt                                    22

<210> SEQ ID NO 20
<211> LENGTH: 21
<212> TYPE: DNA
<213> ORGANISM: artificial sequence
<220> FEATURE:
<223> OTHER INFORMATION: primer

```
<400> SEQUENCE: 20
ctcatctggc acaactcagc g                                              21

<210> SEQ ID NO 21
<211> LENGTH: 22
<212> TYPE: DNA
<213> ORGANISM: artificial sequence
<220> FEATURE:
<223> OTHER INFORMATION: primer

<400> SEQUENCE: 21
ccagatctat cccaccccaa ca                                             22

<210> SEQ ID NO 22
<211> LENGTH: 24
<212> TYPE: DNA
<213> ORGANISM: artificial sequence
<220> FEATURE:
<223> OTHER INFORMATION: primer

<400> SEQUENCE: 22
ggctgacatc atcagtgacc aaga                                           24

<210> SEQ ID NO 23
<211> LENGTH: 25
<212> TYPE: DNA
<213> ORGANISM: artificial sequence
<220> FEATURE:
<223> OTHER INFORMATION: primer

<400> SEQUENCE: 23
catcacactc tccctttctt gctgt                                          25

<210> SEQ ID NO 24
<211> LENGTH: 24
<212> TYPE: DNA
<213> ORGANISM: artificial sequence
<220> FEATURE:
<223> OTHER INFORMATION: primer

<400> SEQUENCE: 24
aatccccaag tgttcttcct gaac                                           24

<210> SEQ ID NO 25
<211> LENGTH: 23
<212> TYPE: DNA
<213> ORGANISM: artificial sequence
<220> FEATURE:
<223> OTHER INFORMATION: primer

<400> SEQUENCE: 25
taagaactga aaagcgggct tgt                                            23

<210> SEQ ID NO 26
<211> LENGTH: 24
<212> TYPE: DNA
<213> ORGANISM: artificial sequence
<220> FEATURE:
<223> OTHER INFORMATION: primer

<400> SEQUENCE: 26
actaccacat gaacatgatg caca                                           24

<210> SEQ ID NO 27
```

```
<211> LENGTH: 22
<212> TYPE: DNA
<213> ORGANISM: artificial sequence
<220> FEATURE:
<223> OTHER INFORMATION: primer

<400> SEQUENCE: 27
ccattctgct cagcccaagt ag                                               22

<210> SEQ ID NO 28
<211> LENGTH: 22
<212> TYPE: DNA
<213> ORGANISM: artificial sequence
<220> FEATURE:
<223> OTHER INFORMATION: primer

<400> SEQUENCE: 28
acagctccat catgggctac aa                                               22

<210> SEQ ID NO 29
<211> LENGTH: 20
<212> TYPE: DNA
<213> ORGANISM: artificial sequence
<220> FEATURE:
<223> OTHER INFORMATION: primer

<400> SEQUENCE: 29
ccaaggtagg ggctggacag                                                  20

<210> SEQ ID NO 30
<211> LENGTH: 5990
<212> TYPE: DNA
<213> ORGANISM: artificial sequence
<220> FEATURE:
<223> OTHER INFORMATION: Partial intron 3

<400> SEQUENCE: 30
gtgagtcatg gtgctgggag gagggacctg ggagaaaagg gccaaaagct ccatttggtg      60
gggtttccag ggttttgaaa ataaagaca acctgtaatc ccagctactt gggaggttga      120
ggagggaaga tcacttgagg ccaggagttt gagaccagcc tgggcatcat agcaagatcc     180
tcatctctaa aaagtaattt tttctaaatt atccagttgt ggtggcatgc acctgtagtc     240
tcagttactc aggaggctga ggtgtgagtt ggaaggattg tttgagccca ggagttaggg     300
accgagctgg gcaacatagc aagacctcat ctctaaataa ataggtaggt ggatagacag     360
atagatagat agacagacag acagacagac agacaggctg ggtacagtgg ctcacacctg     420
taatcccagc actttgggag gccaaggagg gcagatcacc tgaggtcagg agttcaagac     480
cagcctggtc aacatggggg aacctcatct ctactaaaaa tacaaaattt agctgggcat     540
ggtggcaggc gcctgtaatc ccagctactc aggaggctga ggcaagagaa tcgcttgaac     600
ccgagaggtg gaggttgcag tgaaccgaga tcgcgccatt gcactgcagc ctggggaca     660 agagcaagac ttcatctcaa atttaaaata aagaaaaaag aaagaaaag attgatagat     720 agatagatat ccaaatgagt ttacaaaaat gtggtctgtg caaatgttta aacacaacaa     780
accaatgcct ttaactacta cagtataatc ctgtaggatt gtgctattca tgatataatt     840
atggttatat aaaagtaatt aattctcaga gcctcaccag cagtgggtcc agcaagtttg     900
tacagccagc atcttctttc agtcagtgcg tgtcagtaac tgcatatgtc ctctcattgg     960
gagagcctgt cgaaagtcta aatttgaagg cagctgtgaa ggtaaggcca atccaaatgg    1020
ctctcccaga tcctctgctg taaccctgac cctgagtgag gacatagcca accttcccat    1080
```

```
ctcataggtg agaaagctga tgcctggaga ggggaaggga ctgcccaaga tcacatagca    1140
agatagtggc agaacccaag cgagaaccca cagttccagc ctggcttaga agaaagtgca    1200
ctggacttgg agtcaaaggc tggggtttgc atcccagctc tgccataaat ccctgtgtga    1260
ctctgggcaa tttaacctct tagagcttta gtttcttcat ctgtaatatg agggtagcag    1320
tactaccaca tagggttttg agggagtaat tgaattaatc acatgagatg atgcatgttt    1380
acaaaaaaaa gcatgaagcc cctttactgt gcctcagtgt cccaaggac tttggatttt     1440
actctgagaa atacagggag aactagggag tgttgggcag aggagagcca tgatctgact    1500
tatgttttaa gatactctgg cttctgggtt cagaaaagac tgaaggggca agagaggaag    1560
caggtggaga ccagagcggc agtgattgcc atcatccaga ctcagactag gacaatagct    1620
gtgagagtga tgggaagtgg ttggatcctg actgtatttt aatagcagaa ttgacaggat    1680
ttgctgatag actgcacgtg gggtgggaga gggtcaagat gacttcaagg ttctcatctg    1740
gcacaactca gcggctgctg gtgccattta ctgagatggg gaatgttggg gtgggataga    1800
tctgggaggg aaaacccaga gttcagtgtc gaatgtggta gcgttagggt taaggttggg    1860
ggaggggggg tagagatgtg tatgaaacat cccagtggag acactgaatg gagatgtaca    1920
agtctgaagc ttagtggaaa ggttagggct agggatataa atttgggagt tgttacaata    1980
cagatggtgt ttaaagccat gagacccaag gagatcactc aggagtgagg ataaagagag    2040
atgggaagaa gtctgaggac tgagtcctag aacaccctgc attttagagg ggggacatgt    2100
gtaagagcca gcaaaggaga cagaattgtg cttggagagg caggaggaag cccaggagag    2160
cgtgaggtcc tggaaggcaa ggaaagagag ggccccaggt gggctgaatg ctgctgagag    2220
gtcaagtcgg atgagggctg ggaagtagcc attggatttg gccaggagac cttggcatgc    2280
atggttgtag aggaggatga aggcaacagc ctggcttgac tgattcaaga gcaggagatg    2340
agaaagtgga gacagcatgc aggggcagct ctgccaagga cttttgctata aaggggaaca    2400
gagaaatgga ggagaagcag gagggcaata atccgataga gaggaaaaat ctgatgatac    2460
agaagagaga tgaactgcaa gagtcaagcc tttgagttgg aaagcaggag tgggattttg    2520
agcactgata cctttaggcc gatgcaggga cagttcatct ttttttttt tttatacaac    2580
attttattta aaaaaattat tttcatagaa tacattttca cattagagat tcccattgtg    2640
cggaaataac aatttattac ttatagtttt atatttgtgg acagattgtt ttagaacaag    2700
tagaatacat ttgagaatta aatctcagtt tacaatggat aatatttga tatgtctctg     2760
gggaaacttg cccttaaatg gaacttctgt atcttcagaa gcactccaag cgtttcttcc    2820
taggatttag aaatttataa tatgagatag cagcatttcc taattttaaa atttccctag    2880
tatatgtaac catcagtagg tggtatctac tgactagaga gggaagtttt tgaaaattaa    2940
acactgtcta attttctgca aagttttat tcatgaatta agagtatttc cctttgtcca     3000
ttattcccaa gcaaatatg gaaatttgat catgtactaa tcataataaa gctgattct      3060
ctttaagaga ttgagaaatt aaaaggcaaa agctgatata tcatgtttag ttatattgtg    3120
agtcttataa gaagctggga ggcaacccca ttaactcacc agaatacaga actcagtctc    3180
acaacttaga tataattcct ctcaaacctt ttcctcaaag attaaattct gaaataatc     3240
ttgtgattaa gagaagaagg ctgtccacca atgggcttat ctgttatttc ttccttattg    3300
tgagcttaat ggcatgacaa agcagaggca aagaggcata catcaattct tcaaagtagg    3360
aagtcaaaaa ggtcagagct tccacagcat ggcaacagct ttgcagatgc ccacatcgtg    3420
```

```
atagttgaaa tagcaaagcc cagcaaaggt taaagctgaa aatgccaaaa gccctgcctt   3480
ggcagctttc tgcgaggcat ccccatgaac ataatcagta acaacttgtc caaggcccca   3540
gtgaccatga agagtgaggg ctgcagccag ggaatagtcc gtcgcagagc aaggattcaa   3600
ataagcagcc ggaagcagac ccgggagcaa acactgaca accctctcgc tagtccagtg   3660
gagagatgca gccttggagc cagaatggtg gctcggtgac aagtgtatgt gctgcactcc   3720
acaccattct gggataggtc ggtcctgaag aaatgctgag atatgagcag gtctgaccac   3780
tggagttcgc agcaacagag ctcggcctcc ttgggcaccg caaacggcac tcagcctcca   3840
gggaaccgcc atctcgttcc tgaggcggag agttcatctt aacgagagaa atggcaggga   3900
ctgtgaatag gccggcagat tggtggcgg gtgccacagg ttcagtctcc tgcagggaga   3960
ggagaaaatg ccttactaat tccttgtatt ttctcagaga acaagaggc accgtcatca   4020 gcctcatgtg agggtgggaa ggagggatgg ggtttgcgga gagggaaagt gtggtatggt   4080
catctgtggg agtggaagag agtgagaggg ctgcaggggt gcagcgggac tgcaggctgg   4140
caccagggtc cctagggctt gtagttggtg gaaagtgcat cagtgaccag ggctgtgtgc   4200
agctgctcca ggcaggtgtg gaagaagcag agttgaactt gcccagcctg gagtgctgcc   4260
cagagtgagc ccaaagccca ggggagacca gagatgggc tgtttgcaaa ggaggaagta   4320
taacagtagc ccacaaaatc tgagctggtt aagaaggag agagagtgaa atgggagc    4380 ccagcctggc agcctgggta cacatctcag ctcaacccac actagctgaa tccatttggg   4440 cccttcgtt gacctctctg tgcctcagtt tccctatcta tagaatgggg ataagaataa    4500
ggctacttcc tagggctgtt gtgaggattg aacaagtgac cgaacacttg ttcaattttg   4560
aacactgttc taaagcattt aggacagtgc ctggcatggg gtaagtgttg cggcagtgct   4620
gttattttca tcatcaccat tgttctcagg ctgcgttgat tggagctgct gaagggaggc   4680
aatttaagga agtgagccgg acagatagga ggtggtggtg gttatcaggt gcgatgcttg   4740
aaactgaggc ttcggaggca acagttactg gtaatgacaa ggtctaaggc ttgacagtgg   4800
gtggcagaag tgtaacgcag ggaaagagac gagcggtcaa ggagccgaga gggaaggagt   4860
tgggtggact aagatcattt gtggaagaat gatggagaga aaggctgaag ggcagggct    4920 gacatcatca gtgaccaaga ggcggccggg aggctgagac cacagcaaga aagggagagt   4980
gtgatggcat cttcttcaag ggagctgggg atgtttgggg tggaaaaaag aacaatggtc   5040
tgggagggaa tatgggaaat tttttttttt tttttttttt tttttttga gatggagttt   5100 cgctgttgtc atccaggctg gattgcaatg ttgcaatctt ggctcactgc aacttctgcc   5160
ttccaggttc aagtgattct cctgtctcag cttcccgagt agctgagatt acaggcacac   5220
accaccacgc ctggcttact tttgtatttt tagtagagac ggagttttgc catgttggcc   5280
aggctggtct caaactcctg acctcaggtg atccacccgc cttggcctcc caaagtgctg   5340
ggattagagg tgtgagccac gcgcccagc ctggaagttt gtatttatta attttggtt    5400 gtcttcatct gtgtatgtga ctttaacccc taaatacttc agtgtacatt tctttttttt   5460
tttttctttg agacagagtc ttgctccatc aatcacccag gctggagtgc ggtggtgtga   5520
tctcggctca ctgcaacctc cgcctcctgg attcaagcaa ttcttgtgcc tcaccctccc   5580
gagtagctgg gattagggc atgccaccat gcccagttaa ttttgtatt tttagtagag    5640 atggagtttc accatattgg ccaggctggt cttgagctcc tggcctcagt tgatccacct   5700
gtctcagcct cccaaattgc tgagattaca ggcgtgggcc accataaccg gcctcagtgt   5760
atatttctga tgcagttggg ttctgtatcc ccctccaatc tcatctcgaa ttgtaatccc   5820
```

```
cacgtgttga gggcatgacc tcgtgggagg tgattggatc acaggggtgg ttttccccat    5880
gctgttcttg tgacagtgag tgggttttca ggagagctga tggtttgaaa gtgtggcact    5940
tcctctctct ctttctctct ctctctcacc tgacaccacg taagatgtgc               5990
```

<210> SEQ ID NO 31
<211> LENGTH: 51
<212> TYPE: DNA
<213> ORGANISM: artificial sequence
<220> FEATURE:
<223> OTHER INFORMATION: Breakpoint
<220> FEATURE:
<221> NAME/KEY: misc_feature
<222> LOCATION: (26)..(27)
<223> OTHER INFORMATION: Breakpoint

<400> SEQUENCE: 31

```
ctcacctgcc accacgtaag atgtgccact gttcaggtat tgggatggtg g              51
```

<210> SEQ ID NO 32
<211> LENGTH: 51
<212> TYPE: DNA
<213> ORGANISM: artificial sequence
<220> FEATURE:
<223> OTHER INFORMATION: RHD intron 3 of Fig 5

<400> SEQUENCE: 32

```
ctcacctgac accacgtaag atgtgccttg cttccctttc accttccacc a              51
```

<210> SEQ ID NO 33
<211> LENGTH: 51
<212> TYPE: DNA
<213> ORGANISM: artificial sequence
<220> FEATURE:
<223> OTHER INFORMATION: RHD exon 2/intron 2 of Fig 5

<400> SEQUENCE: 33

```
gttcccttct gggaaggtgg tcatcacact gttcaggtat tgggatggtg g              51
```

<210> SEQ ID NO 34
<211> LENGTH: 12032
<212> TYPE: DNA
<213> ORGANISM: artificial sequence
<220> FEATURE:
<223> OTHER INFORMATION: duplicated region
<220> FEATURE:
<221> NAME/KEY: misc_feature
<222> LOCATION: (1)..(10)
<223> OTHER INFORMATION: End of exon 2
<220> FEATURE:
<221> NAME/KEY: misc_feature
<222> LOCATION: (11)..(5891)
<223> OTHER INFORMATION: Intron 2

<400> SEQUENCE: 34

```
cactgttcag gtattgggat ggtggctgga tcacttctgg gtcatagagg gaatggaccc      60
cgaaaggaca ggttccagaa gatctgggat attgccccct ctctgtctag caccagtgct    120
gtgcaatatt taggacatcc ttatactaaa agattattca ttgtttaaaa ttcaaattaa    180
ctgggcatcc tgtattttac tggacagccc tactccgtgt atcacaagga atccaggcct    240
acattcctcc tgcatccttt ctttcctgtt attgtcgatt atgattttgt aaagttacat    300
aatcaatata agtttatgga aaacgtaaga aggaaacacg ttagacagag agaaatagac    360
atgccacacc tagagagaca ttctattttt ttttttttt ttgagacgga gtttcacttt     420
```

```
tgttgcccag gctggagtgc aatggcgcta tctcggcaca ccacaacctc agccttctgg    480
gttcaagcga ttctcctgcc tcagccgcct gagtagctgg gattacaggc atgtgccacc    540
gcgcctggct gattttgtat ttttagtaga tagggtttc tccgtgttg gtcaggctag     600 tctcaaactc ctgacctcag gtgatccgcc cgcctcggcc tcccaaagtg ctgggattac    660
agacatgagc caccgcgtcc agcctgagag acattctctt gaaagaaag gactttcagc    720 cccctaatgc tgctagacaa taaatagcca tgcctttatt ttcattaaat tacctgtgct    780
ttgtttacat gcatttgtgt gaaatgctaa gaaccatcac aactaatgta tggtgccaga    840
agtcagaata gttgttacct gggcaggagg tggatattga ttaggaagga acacaaaata    900
accgcatggg gtgcagaaaa tgttctctat gttcacctgg gtgatgatta cacatcaagc    960
tatacacgtt ttaaaagggc attggcactt aataggagga agtaggctaa atttttttcct  1020 gaaacattgt tttgttttgt tcaaacctct gaatccctgt gctgcccaga tgatggtaaa   1080
cgtcatccta ggcatcttag ggacctctca aggccattcc agcctcccct tctaagaccc   1140
tgctaaacct ctgggcactg ctgttaaaca tttctctatg agccaggaac tgtgctgagc   1200
actccacaaa tattattttg tttaactctt ccgggtaggg atctaacctg gtatacaggt   1260
aaggaagtgg aagctcagag agggcaaggc acttgcctag ggccacacag ctaagtggtg   1320
gagatggctc caacttttta ttataaccttt tccacatgc tccagagtgc tcagaacatg   1380
aaacacagtt tagccagctc ccgattggcc ctggaggaa aaactttat atatttttct    1440 ttttttaaaag gtttagaggc tgggcatggt ggttcacacc tgtaatccca gtacttttgg   1500
gaaccgaggt gggcagatca cttgagccca gaagtttaag accagcctga ctaacacagt   1560
gagatcctgt ctctgcagaa aatagaaaaa tcagctaggc gtggtggtgt gcacccacag   1620
tcccagctac ttgggaggct gaggcaggag gatcacctga acccagtgag gttgaggctg   1680
agtgagccat gatcgtgcca cttcactcca gcctggacaa cagagtgaga ccctgtctca   1740
aaaaacagtt ttagggggccg ggcgcagtgg ttcatgcctg taatcccagc actttgggag   1800
gccaaggcgg ggggatcatg aggtcaggag atcgagacca tcctggctaa ctcggagaaa   1860
ccctgtctct actaaaaata caaaaaatta gccgggcgtg gtggtgggcg cctgtagtcc   1920
cagccactcg ggaggctgag gcaggagaat ggcgtgaacc cgggaggcgg agtttgcagt   1980
gaaccgagat ggtgccactg cactccagcc tgggtgacag agcgagactc cgtctcaaaa   2040
aaaaaaaaca aaaacagttt taggccaggc gcggtggttc atgcctgtaa tcctagtact   2100
ttaggaggcc tagcaggtgg attacctgag gtcaggagtc cgagaccaac ctgagcaaca   2160
tggtgaaatc ctgtctctac taaaaacaca aaaattagct gggtgtggcg gcaggcacct   2220
gtaatcccag ctactgggga ggctgaggca ggcgaatcac ttgaacccgg gaggcggagg   2280
ctatagtgag ccgagatcgc accattgcac tgtagcctgg gcgacagagt gaggctctgt   2340
ctcaaaaaca aaacaaaaca aaacagtct atgagttaat tcccaccaga attcaataca    2400
cacacgcaca catgcacgca tacacacact gtgtccacct gggaagtgac aaagggcacc   2460
ctgggggatt tcaaatggtg gtggccctgg tttggtgttg ctgccttagc ttaaggtcac    2520
accagccttc agcctcctgc cccacagtct agggctgctc ccctcatctg atgtccacag   2580
ggacctgttt gttcttgact caatctagaa agacgagaag ggagagaagt cactcgcagc   2640
ctgagtgaac tcccctgccc cacccctgac tgcttggatc cccctagggg tgacccctgc   2700
tgaaactggc tccttcctga ccggttcccg tcagggctgt gctgatgggt ggtgcccagg   2760
cctgcccctg gggacggggt actctcccctt ggcaacactc cagcttgtgc cacttgactt   2820
```

```
gggactgatt tggttctgtt ttgagtccct tcaggggagg ggcctatctt attcaacgtt   2880
gttgtttgtt ttcctcacat actgataact tagcaaatgg ctattggagc aaaaatgaaa   2940
ataaacggaa ctctgaagtg ggatgtttta aaattttatt tattttttta gagacagggt   3000
cttgctctgt tgcccagtct ggagtgcagt ggtacaatca tagctcattg cagcctgtgc   3060
ctcctgggct caagtgatcc tcccacctca gcctcctgag ttaaattttt ttacaggcgc   3120
ctgctaccat gccctgctaa tttttgtatt tttagtagac aagggqttc accaggtggg    3180 tcaggttggt ctggaactcc cgacctcaag tgatccacct gcctaggcct cccaaagtac   3240
tgggattaca ggcgtgagcc actgtgtcca gcctaaaact gttttttgaga cagggtctca   3300 ctctgttgtc caggctggag tgaagtggca tgttcatggc tcactcagcc tcaacctcac   3360
tgggttcagg tgatcctcct gcctcagcct cccaagtagc tgggactgtg ggtgcacacc   3420
accacgccta gctgattttt ctattttctg cagagacagg acctcactgt gttgctcagg   3480
ctggtctcaa actcctgggc tcaagtgatc tgcccacctc ggctctgaaa agtactggaa   3540
ttacagcctc ctgagtagct gagaccacag gcacacacca ccacacctag cttttttttt   3600
ttttgctttt tgtagagatg gagtctcact atgttgccca ggctggtctc aaactccagg   3660
ccttaagcaa tcctcccacc tcagcctccc aaagtgcgaa gattacaggt gtgagccacc   3720
attcctggcc ttaaaagtgt gatatttta atgtattttg aaatctgcag gactctccct    3780
agaagataat agcaataacc aactccttta ttgtgcttga cgtatatcaa ctcactttgc   3840
ccttaccgtg gctccagagg cattgggtcc accttataaa tggaggcacc aaggcacaga   3900
gtgattaaat aaattgccca ggatcacaca gccagaaagt gtctgagtca agattccagc   3960
ccaggcagcc tagacctgag agcacgctcc taaccactgc acatcactgt cttagcacct   4020
cctcagcaca aactggccct tgaggaatga ataccgccg ccggcacaca cgctcctgag    4080
ttaagccttt gtcaatgaaa tgaacaccca cttaaaagga ataacctgtc caggcacgat   4140
ggaacattga gtaaccccttt attctaaatt cctggtccct gtaagactcc ttccccatgc   4200
ccttgccctt ttctgacctt cccctaaagt ccttgaggct taagcgggca tagtctgcag   4260
caaacactgg ggaagctgag tccagacttc agagcacagg ctttggatct aggccagctg   4320
gatttgaacc tcacatttgt gatcagctgg catgactgtt tccaaaaagt ccatttaat    4380 cctctacgtg accctctgta aaatgggata ctgaatggtg agctagcacg attttacaga   4440
gagtgaattt ttttttgtgtg tgtgtgaggc agtcttactc tgttgcccag gctggagtgc   4500
agtggtgcag tctcggccca ctgaaacctc tgcctcccgg gttcaagcga ctgccatgcc   4560
tcagcctcga gagtggctgg gattacaagc atgcaccacc atgcccgggt aattttttgta  4620 tttttagttg agacagagtt tcaccatgtt ggccaggcca ctcttgaacc cctgqcctca   4680 agtgatccac ctgccttggc ctcccaaagt gctgggagta caggcatgag ccactgcacc   4740
cagccttata gggttaaaat ttaaaagagg tgatgctgtt acaagcctgt tttacaaaat   4800
gctcttataa taaatcatta tcatcactgt tgctgtggtt gtagcatcat catcattaac   4860
tcccagaggg aggagggagt ctcagagcaa gctgctcagg ggagactgga tgtccatgga   4920
ttgtccagct cagtaccact tcctccagga agtcctccct gataagtcca gtcagcatca   4980
ccctctcctt ccaatgaacc ccactagcct tgtgatatca cagatattct tagttgacag   5040
gctcatggtg tagcctgtct agatcataag tacatttttt ttttttttgg atcataagta   5100
tcttcaagac caaaataatt ttctactcct gagcatgctc attggtcaaa ggaaggaagg   5160
```

```
aatcataata gcgttaataa ggctagcgtc ttttcagaag ttggttcttt gtgccagtct    5220
tggtgctaga cacaccgata ggaagaatac tccttcacat ccccaggaca ccaacatggg    5280
atacgtttga tcatcattct taatttgcag aaggagaaat aggctcagtg agatgaaata    5340
gccactccag tggcaaggct gggactggaa gccggcttg tcctgattcc aaatccagtt     5400
tctttccact gccacggaga cggagagaag ggacagtggc cccagatggg gatggggtga    5460
ctggatgtgg gcaggcctgc gggggaagag tgccctctgt tgagcatccg aatgatggca    5520
gcagaaaaga agactgggca gaatcccagt tatcagatcc cctgagggaa cagtcacccc    5580
gatcaccctc agtcagatga gtgtgtgtag atcaatgcct catagatgaa ggcactgagg    5640
cacagagtgg ttaagtcatc tgccagacca catggctcag ggtgcagagg ccaccttaac    5700
gggagaagag atggtcactc cactctgcag catcagcgcc caggtgggta gaaatcttgt    5760
cttctattcc cacagaaagt aggtgcccaa cagtgtttgt tgaaagaatg aatgaatgaa    5820
tgaatgaatg aatgaatgag tgagaggcat ccttccttct cagtcgtcct ggctctccct    5880
ctctccccca gtattcggct ggccaccatg agtgctttgt cggtgctgat ctcagtggat    5940
gctgtcttgg ggaaggtcaa cttggcgcag ttggtggtga tggtgctggt ggaggtgaca    6000
gctttaggca acctgaggat ggtcatcagt aatatcttca acgtgagtca tgtgctgggt    6060
aggagggacc tgggagaaaa gggccaaaag ctccatttgg tggggttttcc agggttttga    6120 aaaataaaga caacctgtaa tcccagctac ttgggaggtt gaggagggaa gatcacttga    6180
ggccaggagt ttgagaccag cctgggcatc atagcaagat cctcatctct aaaaagtaat    6240
tttttctaaa ttatccagtt gtggtggcat gcacctgtag tctcagttac tcaggaggct    6300
gaggtgtgag ttggaaggat tgtttgagcc caggagttag ggaccgagct gggcaacata    6360
gcaagacctc atctctaaat aaataggtag gtggatagac agatagatag atagacagac    6420
agacagacag acagacaggc tgggtacagt ggctcacacc tgtaatccca gcactttggg    6480
aggccaagga gggcagatca cctgaggtca ggagttcaag accagcctgg tcaacatggg    6540
ggaacctcat ctctactaaa aatacaaaat ttagctgggc atggtggcag gcgcctgtaa    6600
tcccagctac tcaggaggct gaggcaagag aatcgcttga acccgagagg tggaggttgc    6660
agtgaaccga gatcgcgcca ttgcactgca gcctggggga caagagcaag acttcatctc    6720
aaatttaaaa taagaaaaa agaaagaaa agattgatag atagatagat atccaaatga     6780
gtttacaaaa atgtggtctg tgcaaatgtt taaacacaac aaaccaatgc ctttaactac    6840
tacagtataa tcctgtagga ttgtgctatt catgatataa ttatggttat ataaaagtaa    6900
ttaattctca gagcctcacc agcagtgggt ccagcaagtt tgtacagcca gcatcttctt    6960
tcagtcagtg cgtgtcagta actgcatatg tcctctcatt gggagagcct gtcgaaagtc    7020
taaatttgaa ggcagctgtg aaggtaaggc caatccaaat ggctctccca gatcctctgc    7080
tgtaaccctg accctgagtg aggacatagc caaccttccc atctcatagg tgagaaagct    7140
gatgcctgga gagggaagg gactgcccaa gatcacatag caagatagtg gcagaaccca    7200
agcgagaacc cacagttcca gcctggctta aagaaagtg cactggactt ggagtcaaag    7260 gctgggttt gcatcccagc tctgccataa atccctgtgt gactctgggc aatttaacct    7320
cttagagctt tagtttcttc atctgtaata tgagggtagc agtactacca catagggttt    7380
tgagggagta attgaattaa tcacatgaga tgatgcatgt ttacaaaaaa aagcatgaag    7440 ccccttact gtgcctcagt gtcccaaagg actttggatt ttactctgag aaatacaggg     7500
agaactaggg agtgttgggc agaggagagc catgatctga cttatgtttt aagatactct    7560
```

```
ggcttctggg ttcagaaaag actgaagggg caagagagga agcaggtgga gaccagagcg    7620
gcagtgattg ccatcatcca gactcagact aggacaatag ctgtgagagt gatgggaagt    7680
ggttggatcc tgactgtatt ttaatagcag aattgacagg atttgctgat agactgcacg    7740
tggggtggga gagggtcaag atgacttcaa ggttctcatc tggcacaact cagcggctgc    7800
tggtgccatt tactgagatg gggaatgttg gggtgggata gatctgggag ggaaaaccca    7860
gagttcagtg tcgaatgtgg tagcgttagg gttaaggttg gggaggggg ggtagagatg    7920 tgtatgaaac atcccagtgg agacactgaa tggagatgta caagtctgaa gcttagtgga    7980
aaggttaggg ctagggatat aaatttggga gttgttacaa tacagatggt gtttaaagcc    8040
atgagaccca aggagatcac tcaggagtga ggataaagag agatgggaag aagtctgagg    8100
actgagtcct agaacaccct gcattttaga gggggacat gtgtaagagc cagcaaagga    8160
gacagaattg tgcttggaga ggcaggagga agcccaggag agcgtgaggt cctggaaggc    8220
aaggaaagag agggccccag gtgggctgaa tgctgctgag aggtcaagtc ggatgagggc    8280
tgggaagtag ccattggatt tggccaggag accttggcat gcatggttgt agaggaggat    8340
gaaggcaaca gcctggcttg actgattcaa gagcaggaga tgagaaagtg gagacagcat    8400
gcaggggcag ctctgccaag gactttgcta taaaggggaa cagagaaatg gaggagaagc    8460
aggagggcaa taatccgata gagaggaaaa atctgatgat acagaagaga gatgaactgc    8520
aagagtcaag cctttgagtt ggaaagcagg agtgggattt tgagcactga tacctttagg    8580
ccgatgcagg gacagttcat ctttttttt tttttataca acattttatt taaaaaaatt    8640 atttttcatag aatacatttt cacattagag attcccattg tgcggaaata acaatttatt    8700
acttatagtt ttatatttgt ggacagattg ttttagaaca agtagaatac atttgagaat    8760
taaatctcag tttacaatgg ataatatttt gatatgtctc tggggaaact tgcccttaaa    8820
tggaacttct gtatcttcag aagcactcca agcgtttctt cctaggattt agaaatttat    8880
aatatgagat agcagcattt cctaatttta aaatttccct agtatatgta accatcagta    8940
ggtggtatct actgactaga gagggaagtt tttgaaaatt aaacactgtc taattttctg    9000
caaagttttt attcatgaat taagagtatt tccctttgtc cattattccc aaggcaaata    9060
tggaaatttg atcatgtact aatcataata aagctggatt ctctttaaga gattgagaaa    9120
ttaaaaggca aaagctgata tatcatgttt agttatattg tgagtcttat aagaagctgg    9180
gaggcaaccc cattaactca ccagaataca gaactcagtc tcacaactta gatataattc    9240
ctctcaaacc ttttcctcaa agattaaatt ctgaaaataa tcttgtgatt aagagaagaa    9300
ggctgtccac caatgggctt atctgttatt tcttccttat tgtgagctta atggcatgac    9360
aaagcagagg caaagaggca tacatcaatt cttcaaagta ggaagtcaaa aaggtcagag    9420
cttccacagc atggcaacag ctttgcagat gcccacatcg tgatagttga aatagcaaag    9480
cccagcaaag gttaaagctg aaaatgccaa aagccctgcc ttggcagctt tctgcgaggc    9540
atccccatga acataatcag taacaacttg tccaaggccc cagtgaccat gaagagtgag    9600
ggctgcagcc agggaatagt ccgtcgcaga gcaaggattc aaataagcag ccggaagcag    9660
acccgggagc aaaacactga caaccctctc gctagtccag tggagagatg cagccttgga    9720
gccagaatgg tggctcggtg acaagtgtat gtgctgcact ccacaccatt ctgggatagg    9780
tcggtcctga agaaatgctg agatatgagc aggtctgacc actggagttc gcagcaacag    9840
agctcggcct ccttgggcac cgcaaacggc actcagcctc cagggaaccg ccatctcgtt    9900
```

```
cctgaggcgg agagttcatc ttaacgagag aaatggcagg gactgtgaat aggccggcag    9960
atttggtggc gggtgccaca ggttcagtct cctgcaggga gaggagaaaa tgccttacta   10020
attccttgta ttttctcaga gaaacaagag gcaccgtcat cagcctcatg tgagggtggg   10080
aaggagggat ggggtttgcg gagagggaaa gtgtggtatg gtcatctgtg ggagtggaag   10140
agagtgagag ggctgcaggg gtgcagcggg actgcaggct ggcaccaggg tccctagggc   10200
ttgtagttgg tggaaagtgc atcagtgacc agggctgtgt gcagctgctc caggcaggtg   10260
tggaagaagc agagttgaac ttgcccagcc tggagtgctg cccagagtga gcccaaagcc   10320
caggggagac cagagatggg gctgtttgca aaggaggaag tataacagta gcccacaaaa   10380
tctgagctgg ttaagaaagg agagagagtg aaaatgggga gcccagcctg gcagcctggg   10440
tacacatctc agctcaaccc acactagctg aatccatttg ggccccttcg ttgacctctc   10500
tgtgcctcag tttccctatc tatagaatgg ggataagaat aaggctactt cctagggctg   10560
ttgtgaggat tgaacaagtg accgaacact tgttcaattt tgaacactgt tctaaagcat   10620
ttaggacagt gcctggcatg gggtaagtgt tgcggcagtg ctgttatttt catcatcacc   10680
attgttctca ggctgcgttg attggagctg ctgaagggag gcaatttaag gaagtgagcc   10740
ggacagatag gaggtggtgg tggttatcag gtgcgatgct tgaaactgag gcttcggagg   10800
caacagttac tggtaatgac aaggtctaag gcttgacagt gggtggcaga agtgtaacgc   10860
agggaaagag acgagcggtc aaggagccga gaggaaggga gttgggtgga ctaagatcat   10920
ttgtggaaga atgatggaga gaaaggctga agggcagggg ctgacatcat cagtgaccaa   10980
gaggcggccg ggaggctgag accacagcaa gaaagggaga gtgtgatggc atcttcttca   11040
agggagctgg ggatgtttgg ggtggaaaaa agaacaatgg tctgggaggg aatatgggaa   11100
atttttttt tttttttttt tttttttttt gagatggagt ttcgctgttg tcatccaggc   11160
tggattgcaa tgttgcaatc ttggctcact gcaacttctg ccttccaggt tcaagtgatt   11220
ctcctgtctc agcttcccga gtagctgaga ttacaggcac acaccaccac gcctggctta   11280
ctttttgtatt tttagtagag acggagtttt gccatgttgg ccaggctggt ctcaaactcc   11340
tgacctcagg tgatccaccc gccttggcct cccaaagtgc tgggattaga ggtgtgagcc   11400
accgcgccca gcctggaagt ttgtatttat taattttttgg ttgtcttcat ctgtgtatgt   11460
gactttaacc cctaaatact tcagtgtaca tttctttttt ttttttcttt tgagacagag   11520
tcttgctcca tcaatcaccc aggctggagt gcggtggtgt gatctcggct cactgcaacc   11580
tccgcctcct ggattcaagc aattcttgtg cctcaccctc ccgagtagct gggattaggg   11640
gcatgccacc atgcccagtt aatttttgta ttttagtag agatggagtt tcaccatatt   11700
ggccaggctg gtcttgagct cctggcctca gttgatccac ctgtctcagc ctcccaaatt   11760
gctgagatta caggcgtggg ccaccataac cggcctcagt gtatatttct gatgcagttg   11820
ggttctgtat ccccctccaa tctcatctcg aattgtaatc cccacgtgtt gagggcatga   11880
cctcgtggga ggtgattgga tcacagggggt ggttttccccc atgctgttct tgtgacagtg   11940
agtgggtttt caggagagct gatggtttga aagtgtggca cttcctctct ctctttctct   12000
ctctctctca cctgacacca cgtaagatgt gc                                 12032
```

<210> SEQ ID NO 35
<211> LENGTH: 30
<212> TYPE: DNA
<213> ORGANISM: artificial sequence
<220> FEATURE:
<223> OTHER INFORMATION: narrow breakpoint region

```
<220> FEATURE:
<221> NAME/KEY: misc_feature
<222> LOCATION: (15)..(16)
<223> OTHER INFORMATION: breakpoint

<400> SEQUENCE: 35
ccacgtaaga tgtgccactg ttcaggtatt                                           30

<210> SEQ ID NO 36
<211> LENGTH: 21
<212> TYPE: DNA
<213> ORGANISM: artificial sequence
<220> FEATURE:
<223> OTHER INFORMATION: primer

<400> SEQUENCE: 36
cttgggcttc ctcacctcga g                                                    21

<210> SEQ ID NO 37
<211> LENGTH: 22
<212> TYPE: DNA
<213> ORGANISM: artificial sequence
<220> FEATURE:
<223> OTHER INFORMATION: primer

<400> SEQUENCE: 37
cgaacacgta gatgtgcatc at                                                   22

<210> SEQ ID NO 38
<211> LENGTH: 18
<212> TYPE: DNA
<213> ORGANISM: artificial sequence
<220> FEATURE:
<223> OTHER INFORMATION: primer

<400> SEQUENCE: 38
atcatgccat tgccggct                                                        18

<210> SEQ ID NO 39
<211> LENGTH: 19
<212> TYPE: DNA
<213> ORGANISM: artificial sequence
<220> FEATURE:
<223> OTHER INFORMATION: primer

<400> SEQUENCE: 39
gagccaagta cctgccggg                                                       19

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
tctccatgtc gtcccagttg                                                      20

<210> SEQ ID NO 41
<211> LENGTH: 20
<212> TYPE: DNA
<213> ORGANISM: artificial sequence
<220> FEATURE:
<223> OTHER INFORMATION: primer
```

```
<400> SEQUENCE: 41
agtcttcccc tccatcgttg                                               20
```

RHD GENE ALLELE ASSOCIATED WITH A WEAK D PHENOTYPE AND ITS USES

CROSS-REFERENCE TO RELATED APPLICATION

This application is the U.S. national stage application of International Patent Application No. PCT/EP2018/055529, filed Mar. 7, 2018.

The Sequence Listing for this application is labeled "Seq-List.txt" which was created on Aug. 13, 2019 and is 31 KB. The entire content of the sequence listing is incorporated herein by reference in its entirety.

FIELD OF THE INVENTION

The present invention relates to a novel allele of Rh D antigen contributing to the weak D phenotype, to methods and kits for detecting this Rh D antigen.

BACKGROUND OF THE INVENTION

Among the 36 human blood group systems reported so far and officially acknowledged by the International Society of Blood Transfusion (ISBT, www.isbtweb.org), Rh system is the most complex and polymorphic system. It involves two paralogous genes, RHD and RHCE, each encoding a transmembrane protein (RhD and RhCE, respectively) expressed at the surface of erythroid cell lineage. These proteins express 54 antigens (www.isbtweb.org). Antigen D, carried by RhD, is the most immunogenic antigen and may induce alloimmunization (i.e. production of antibodies directed against an antigen) when introduced in a D-negative (D−) individual with two major, potential risks:

Hemolytic transfusion reaction (HTR), with severe clinical outcomes, may occur in an alloimmunized D− recipient transfused with a D+ red blood cell unit;

Hemolytic disease of the fetus and newborn (HDFN) may occur in an alloimmunized D− pregnant woman with a D+ fetus with potential dramatic consequences.

Rh status is thus of major interest in Public Health. In routine it is determined by serological analyses with different panels of antibodies. Although these tests are relevant most of the time, ambiguity and/or discrepancy with different panels of antibodies may be observed in some circumstances. Then it is necessary to use molecular analysis to identify genetic variations and predict Rh status.

Since RHD and RHCE genes were both discovered in the early nineties, more than 300 different alleles have been reported in the literature (www.rhesusbase.info/), involving different molecular mechanisms: single-nucleotide variations, short insertions/deletions, rearrangements and microdeletions. These variants, which are typically distributed in an ethnicity-dependent manner, induce a large phenotypic variability including quantitative and/or qualitative modification(s) of antigen expression. This variability is characterized serologically by ambiguity/discrepancy as indicated above.

Identification/knowledge of the specific molecular bases of RHD variability in populations is thus of the main interest for 1/ the implementation of the genotyping strategy and 2/ the management of transfusions in patients/pregnant women. Indeed depending on their genotype, donors/patients are considered as D− or D+ and thus managed differently.

Many studies dealing with identification and characterization of many specific variants in Caucasians, Africans and Asians have been published. To date the global distribution of variants is well known in each population, although numerous others are likely to be found in the future.

Conversely, populations of other origins, such as Indians, have not been documented in terms of molecular genetics, while several phenotype studies have reported the incidence of RhD-negative individuals in Northern India (6.6%), Delhi (6.3%) and Mumbai (3-7.5%), but also weak D (~0.2%) (Kumar et al, 2005, *Med J Armed Forces India*, 61, 348-350) and partial D (>0.15%) antigen carriers. Phenotypic data in terms of D antigen density and their distribution in different castes and tribes of the Indian population in the Mumbai region have also been provided.

The proper identification of weak D subjects in Indian population is clinically relevant. Therefore, development of an Indian-specific genotyping strategy at the laboratory level may have major consequences, in particular for the clinical management of transfusions and pregnancies at risk in India.

SUMMARY OF THE INVENTION

The present invention concerns a duplication of exon 3 of the RHD gene which is indicative of a weak D phenotype in a subject, in particular a subject from the Indian population. Then, the present invention relates to a method of genotyping, especially RHD genotyping, based on the determination of the presence of a duplication of exon 3 of the RHD gene, said duplication being indicative of a weak D phenotype.

Accordingly, the present invention relates to a method for detecting the presence of a duplication of exon 3 of the RHD gene in a DNA sample comprising contacting a probe or a set of primers specific to the duplication of exon 3 of the RHD gene with the DNA sample and detecting a hybridization of the probe or an amplification product of the set of primers, the detection of said hybridization or said amplification product being respectively indicative of the presence of a duplication of exon 3 of the RHD gene in the DNA sample, wherein a probe specific to the duplication of exon 3 of the RHD gene specifically hybridizes a portion of the RHD gene specific to the duplication of exon 3 comprising at least 5, 6, 7, 8, 9 or 10 nucleotides upstream and downstream of the breakpoint of SEQ ID NO: 31, a sequence having at least 90, 95 or 99% of identity with SEQ ID NO: 31 or a complementary sequence thereof and; a set of primers specific to the duplication of exon 3 of the RHD gene produces an amplification product only when a duplication of exon 3 is present.

The present invention also relates to a method for determining RHD genotype or for detecting a weak D phenotype, comprising detecting the presence of a duplication of exon 3 of the RHD gene in a DNA sample according to the present invention, wherein the presence of a duplication of exon 3 of the RHD gene in the DNA sample is indicative of a weak D phenotype.

Preferably, the probe or the amplification product has a sequence comprising at least 5, 6, 7, 8, 9 or 10 nucleotides upstream and downstream of the breakpoint of SEQ ID NO: 31 or the complementary sequence thereof, the probe or amplification product having at least 20 nucleotides in length.

In one embodiment, the method comprises
a) contacting a set of primers specific to the duplication of exon 3 of the RHD gene with the DNA sample and an amplification reaction mixture;
b) producing the amplification product using a primer-dependent DNA amplification reaction; and c) detecting the amplification product, the detection of said amplification product being indicative of the presence of a duplication of exon 3 of the RHD gene in the DNA sample.

Optionally, the step b) is a multiplex amplification such as multiplex PCR or multiplex LPA (Ligation-dependent Probe Amplification).

More particularly, the primer-dependent DNA amplification reaction is a PCR reaction, preferably multiplex PCR.

Optionally, the method further comprises the detection of the presence of one or several exons of the RHD gene, in particular exon 5 and/or exon 10 of the RHD gene.

The present invention further relates to a kit for detecting the presence of a duplication of exon 3 of the RHD gene in a DNA sample, for determining RHD genotype or for detecting a weak D phenotype, wherein the kit comprises a probe or a set of primers specific to the duplication of exon 3 of the RHD gene in a DNA sample, wherein a probe specific to the duplication of exon 3 of the RHD gene specifically hybridizes a portion of the RHD gene specific to the duplication of exon 3 comprising at least 5, 6, 7, 8, 9 or 10 nucleotides upstream and downstream of the breakpoint of SEQ ID NO: 31, a sequence having at least 90, 95 or 99% of identity with SEQ ID NO: 31 or a complementary sequence thereof and; a set of primers specific to the duplication of exon 3 of the RHD gene produces an amplification product only when a duplication of exon 3 is present.

In one embodiment of the methods or kit, the specific set of primers comprises a forward primer in partial intron 3 located upstream of the breakpoint, especially of SEQ ID NO: 30, and a reverse primer in the Exon2/intron2 region of the duplicated region located downstream of the breakpoint, especially positions 1-5891 of SEQ ID NO: 34.

More specifically, the specific set of primers comprises
a forward primer in partial intron 3 located within 1000 bp upstream of the breakpoint, preferably within 500 bp upstream of the breakpoint, and more preferably within 200 bp upstream of the breakpoint; and
a reverse primer in the Exon2/intron2 region of the duplicated region located within 1000 bp downstream of the breakpoint, preferably with 500 bp downstream of the breakpoint, and more preferably within 200 bp downstream of the breakpoint.

For instance, the set of primers may include:
a forward primer comprising, or consisting of, a sequence selecting from the group consisting of:

```
                                      (SEQ ID NO: 3)
         ACGTGTTGAGGGCATGACCTC (SEQ ID NO: 20)
         CTCATCTGGCACAACTCAGCG
and
                                      (SEQ ID NO: 22)
         GGCTGACATCATCAGTGACCAAGA
``` and
a reverse primer comprising, or consisting of, a sequence selecting from the group consisting of:

```
                                      (SEQ ID NO: 4)
         GCCTGGATTCCTTGTGATACACG (SEQ ID NO: 17)
         TTCTTAGCATTTCACACAAATGCATG
```

```
                                      (SEQ ID NO: 19)
         GATCACCTGAACCCAGTGAGGT.
```

More specifically, the set of primers may include:
a forward primer comprising, or consisting of, a sequence

```
                                      (SEQ ID NO: 3)
         ACGTGTTGAGGGCATGACCTC;
``` and
a reverse primer comprising, or consisting of, a sequence

```
                                      (SEQ ID NO: 4)
         GCCTGGATTCCTTGTGATACACG.
```

The kit may further comprise one or several elements selected in the group consisting of:
a set of primer or a probe specific to exon 5 of the RHD gene;
a set of primer or a probe specific to exon 10 of the RHD gene; and
an amplification reaction mixture.

For instance, the kit comprises the following primers:
a primer comprising, or consisting of, a sequence

```
                                      (SEQ ID NO: 3)
         ACGTGTTGAGGGCATGACCTC;
``` a primer comprising, or consisting of, a sequence

```
                                      (SEQ ID NO: 4)
         GCCTGGATTCCTTGTGATACACG;
``` a primer comprising, or consisting of, a sequence

```
                                      (SEQ ID NO: 1)
         ATACCTTTGAATTAAGCACTTCACAGAG;
``` a primer comprising, or consisting of, a sequence

```
                                      (SEQ ID NO: 2)
         ACTGTGACCACCCAGCATTCTA;
``` a primer comprising, or consisting of, a sequence

```
                                      (SEQ ID NO: 5)
         AGGCTGTTTCAAGAGATCAAGCCA;
``` and
a primer comprising, or consisting of, a sequence

```
                                      (SEQ ID NO: 6)
         GATGTTGTTATGTGGTACATGGCTG.
```

The present invention relates to the use of a kit according to the present invention for detecting the presence of a duplication of exon 3 of the RHD gene in a DNA sample, for determining RHD genotype or for detecting a weak D phenotype.

Finally, the present invention relates to an isolated or recombinant nucleic acid comprising or consisting of a sequence SEQ ID NO: 35.

DETAILED DESCRIPTION OF THE INVENTION

Figure 1:
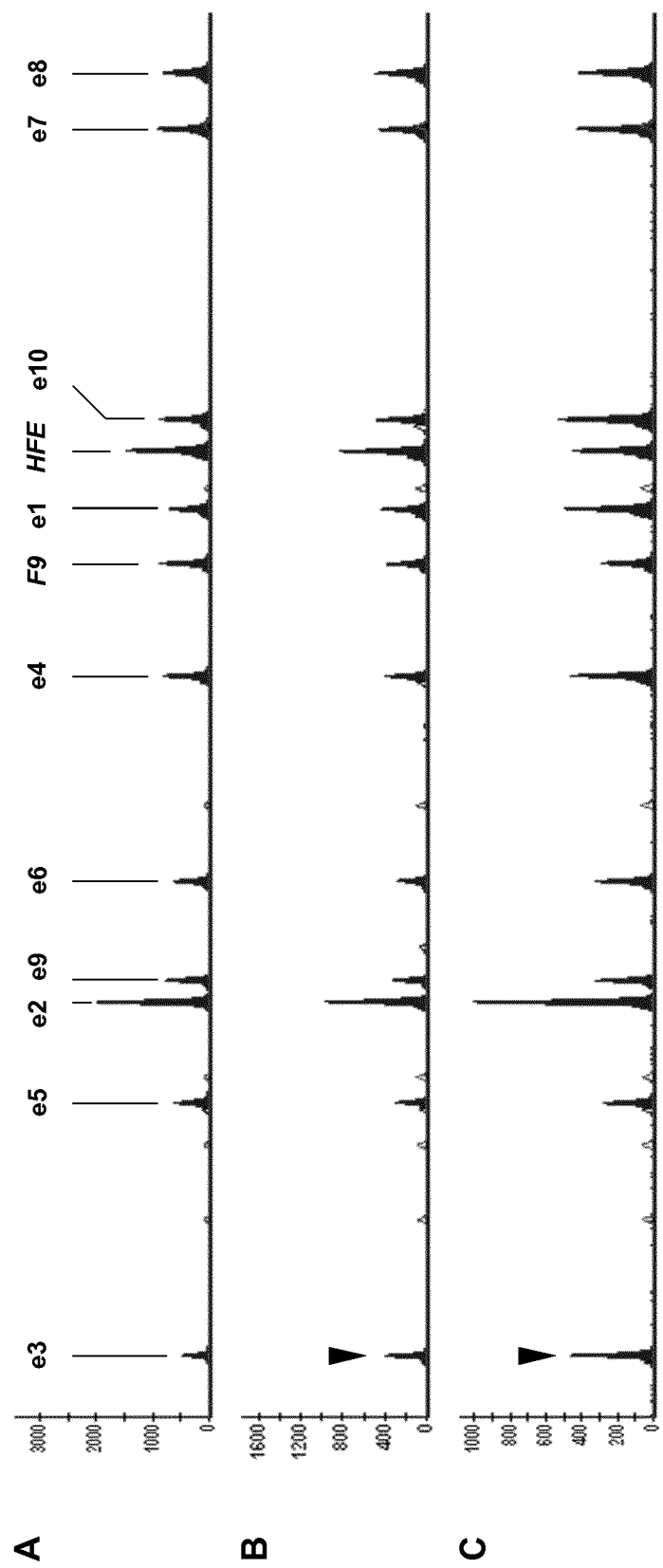
FIG. 1. RHD exon 3 is duplicated in some Indian weak D individuals. Typical RHD QMPSF profiles obtained with (A) a hemizygous, wild-type RHD calibrator (Rh C/c, E/e phenotype: Ccee); (B) a hemizygous (exon 3 duplication) sample (Ccee); and (C) a homozygous (exon 3 duplication) sample (CCee). Arrowheads indicate copy number variation (CNV) of exon 3 in the samples; e1 to e10: RHD exons 1 to 10.

In the course of a collaborative project, which aim was to analyze RHD gene variants in weak D Indians, a novel RHD allele characterized by an original mutational mechanism, "RHD exon 3 duplication", was identified by the inventors. This population-specific variant allele has been found in ~60% samples presenting with a weak D phenotype, namely 0.2% of the whole Indian population. From a phenotypic point of view, people harboring this allele may be considered as D+.

Accordingly, this novel RHD allele is the main cause of weak D phenotype in the Indian population.

Definitions

The RHD gene encodes the Rh D antigen. This gene is referenced in the following public databases: UniProt #Q02161, GeneCards #RHD, Gene ID #6007, and HGNC #10009. "RHD" refers to Rhesus D or Rhesus D antigen.

A Weak D phenotype is a group of RhD+ phenotypes with a reduced expression of Rh D antigen on the red blood cells' surface.

"Breakpoint" refers to the junction between the partial intron 3 in 5' with the partial exon 2 in 3' when a duplication of exon 3 in the RHD gene is present. In particular, the position of Breakpoint could defined as:

in position following the position 5990 of intron 3 of the RHD gene, at the end of partial intron 3 as shown in SEQ ID NO: 30; and/or between positions 26 and 27 in SEQ ID NO: 31, showing the junction sequence between the partial intron 3 in 5' with the partial exon 2 in 3' of the RHD gene; and/or in position before the duplicated region the RHD gene, before the partial exon 2, before the position 1 of SEQ ID NO: 34.

By "partial intron 3" is intended to refer to the part of intron 3 located before the Breakpoint. A sequence of partial intron 3 is shown in SEQ ID NO: 30.

By "Exon2/intron2 region of the duplicated region" is intended to refer to the part of exon 2 and the intron 2 which is duplicated. A sequence of Exon2/intron2 region of the duplicated region is shown in SEQ ID NO: 34 in positions 1-5891.

By "duplicated region" is intended to refer to the part of exon 2, intron 2, exon 3 and intron 3 which is duplicated. A sequence of the duplicated region is shown in SEQ ID NO: 34.

The term "genotype" as used herein, refers to a description of the alleles of a gene or a plurality of genes contained in an individual or in a sample from said individual.

The term "DNA sample" refers to a sample containing human genomic DNA obtained from a subject.

As used herein, the term "subject" refers to a human, including adult, in particular a woman, a child and a human at the prenatal stage in particular a foetus. In a particular aspect, the subject has been classified as Rhesus D− by a classical assay for determining the Rhesus D status, e.g., assays using antibodies directed against Rhesus D antigen, in particular by agglutination reaction.

As used herein, the term "primer" refers to a synthetically or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such polymerases or reverse transcriptases require the presence of a primer that may be extended to initiate such nucleic acid synthesis. A primer is typically 11 bases or longer; most preferably, a primer is 17 bases or longer, although shorter or longer primers may be used depending on the need. As will be appreciated by those skilled in the art, the oligonucleotides disclosed herein may be used as one or more primers in various extension, synthesis, or amplification reactions.

Typically, a PCR reaction employs a pair of amplification primers including an "upstream" or "forward" primer and a "downstream" or "reverse" primer, which delimit a region of the RNA or DNA to be amplified.

The terms "complementarity" and "complementary" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100 percent complementarity refers to the situation in which each nucleotide unit of one polynucleotide strand or region can hydrogen bond with each nucleotide unit of a second polynucleotide strand or region.

As used herein, the term "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences.

A "labeled probe" or "labeled primer" refers to a nucleic acid, especially single-stranded nucleic acid, conjugated to a compound that produces a detectable signal. Suitable labels include, but are not limited to, radioactive molecule, fluorescent molecule, mass label, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant and electrical conductivity.

As used herein, the terms "amplification", "nucleic acid amplification", or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. For instance, other types of amplification reactions contemplated include both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR. The term "amplifying" that typically refers to an "exponential" increase in target nucleic acid may be used herein to describe both linear and exponential increases in the numbers of a select target sequence of nucleic acid.

The term "amplification reaction mixture" and/or "master mix" may refer to an aqueous solution comprising the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, other types of nucleic acid amplification reactions are also contemplated, including both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR.

The term "polymerase chain reaction" or "PCR" as used herein refers to a method for amplifying a DNA sequence using a heat-stable DNA polymerase and a set of amplification primers in a cyclical reaction where the annealing of primers, synthesis of progeny strand DNA and denaturation of the duplexes, are each conducted at different temperatures. Because the newly synthesized DNA strands can subsequently serve as additional templates for the same primer sequences, successive rounds of primer annealing, strand elongation and dissociation produce rapid amplification of the target sequence.

As used herein, the term "DNA polymerase" refers to an enzyme that is essential for elongation of amplification primers in nucleic acid templates. The skilled person may easily choose a convenient polymerase enzyme based on its characteristics such as efficiency, processivity or fidelity. Preferably, the polymerase is a high-fidelity and heat-stable polymerase.

The term "amplicon" or "amplification product" as used herein refers to a fragment of DNA spanned within a pair of amplification primers, this fragment being amplified exponentially by a DNA polymerase. An amplicon can be single-stranded or double-stranded.

As used herein, the term "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm-.nih.gov/ or http://www.ebi.ac.uk/Tools/emboss/). Those skilled in the art can determine appropriate parameters for measuring alignment, including any algorithms needed to achieve maximal alignment over the full length of the sequences being compared. By "a sequence at least x % identical to a reference sequence", it is intended that the sequence is identical to the reference sequence or differs from the reference sequence by up to 100−x nucleotide alterations per each 100 nucleotides of the reference sequence.

The terms "low stringency", "medium stringency", "medium/high stringency", "high stringency" and "very high stringency" refer to conditions of hybridization. Suitable experimental conditions for determining hybridization between a nucleotide probe and a homologous DNA or RNA sequence involves presoaking of the filter containing the DNA fragments or RNA to hybridize in 5×SSC (Sodium chloride/Sodium citrate for 10 min, and prehybridization of the filter in a solution of 5×SSC, 5×Denhardt's solution, 0.5% SDS and 100 μg/ml of denatured sonicated salmon sperm DNA, followed by hybridization in the same solution containing a concentration of 10 ng/ml of a random-primed $^{32}$P-dCTP-labeled (specific activity $>1\times10^9$ cpm/μg) probe for 12 hours at ca. 45° C. (Feinberg and Vogelstein, 1983). For various stringency conditions the filter is then washed twice for 30 minutes in 2×SSC, 0.5% SDS and at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Preferably, the methods of the invention are in vitro methods.

The present invention relates to a method for testing the presence of a duplication of exon 3 in the RHD gene. Accordingly, the present invention relates to a method for detecting a weak D phenotype and the method comprises testing the presence of a duplication of exon 3 in the RHD gene. More generally, the present invention relates to a method for RHD genotyping, the method comprises testing the presence of a duplication of exon 3 in the RHD gene. Indeed, as discussed before, a duplication of exon 3 in the RHD gene is indicative of a weak D phenotype and a weak D phenotype is generally classified as a Rhesus D$^+$ status.

The present invention further relates to a kit comprising means for detecting the presence of a duplication of exon 3 in the RHD gene and the use of the kit for testing the presence of a duplication of exon 3 in the RHD gene, for detecting a weak D phenotype or for RHD genotyping.

The presence of a duplication of exon 3 in the RHD gene can be detected by any suitable means available to the person skilled in the art. In particular, the suitable means can be a probe specific to the duplication of exon 3 in the RHD gene, a set of primers specific to the duplication of exon 3 in the RHD gene or a combination thereof.

For instance, the method may comprise contacting a probe or a set of primers specific to the duplication of exon 3 of the RHD gene with the DNA sample and detecting a hybridization of the probe or an amplification product of the set of primers, the detection of said hybridization or said amplification product being respectively indicative of the presence of a duplication of exon 3 of the RHD gene in the DNA sample.

The DNA sample is prepared from a biological sample, preferably a sample comprising erythroid tissue. The biological sample can be whole blood, plasma, serum, urine, cervical mucus, amniotic fluid or sample, or chorionic villus sample. The sample is from human origin. In a preferred embodiment, the biological sample is whole blood, plasma, or serum. In particular, the sample can be a maternal sample or a foetal sample. The sample may also provide from a sample of a blood bank, in particular from a sample from blood unit. In a particular embodiment, the sample is from an individual with is Indian (Indian population) or has an individual of Indian descent. As used herein, "an individual of Indian descent" refers to people who have a have ancestors from the geographic region India and surrounding areas including, but not limited to, India, Pakistan, Nepal and Bangladesh. Preferably, at least one ancestor is from India or surrounding areas. Indian population may further include India, Pakistan, Nepal and Bangladesh. In a particular embodiment, the sample comes from an individual, a blood bank sample or immunohematology laboratories which has been shown weaker or discrepant results by a classical assay for determining the Rhesus D status, e.g., assays using antibodies directed against Rhesus D antigen, in particular by agglutination reaction with a panel of monoclonal anti-D reagents.

The methods for preparing or extracting a DNA sample from a biological sample are well-known in the art.

In a first embodiment, the present invention relates to a method comprising a) contacting a set of primers specific to the duplication of exon 3 of the RHD gene with the DNA sample and an amplification reaction mixture in conditions suitable for amplification; and b) detecting an amplification product of the set of primers, the detection of said amplification product respectively being indicative of the presence of a duplication of exon 3 of the RHD gene in the DNA sample. Accordingly, step a) is an amplification step.

In a specific embodiment, a set of primers is a pair of primers.

The set or pair of primers is specific to portion of the RHD gene that flanks the breakpoint, in particular suitable for producing an amplification product only when a duplication of exon 3 is present. In a preferred embodiment, the specific set of primers comprises a forward primer in the RHD gene upstream of the breakpoint, and a reverse primer in the RHD gene downstream of the breakpoint. More specifically, the specific set of primers comprises a forward primer in the intron 3 upstream of the breakpoint, and a reverse primer in intron 2 downstream of the breakpoint. A sequence of the intron 3 upstream of the breakpoint is described in SEQ ID NO: 30 and a sequence of the exon 2 and intron 2 downstream of the breakpoint is described in SEQ ID NO: 34, especially positions 1-5891 of SEQ ID NO: 34.

The set or pair of primers is designed so as the amplification product has a sequence comprising at least 5, 6, 7, 8, 9, 10, 15, 20 or 25 nucleotides upstream and downstream of the breakpoint of SEQ ID NO: 31, a sequence having at least 90, 95 or 99% identity with SEQ ID NO: 31 or a complementary sequence thereof. In addition, the set or pair of primers is designed such as the amplification product has an appropriate length, in particular appropriate to the method used for detecting the presence of the amplification product. The size of the amplification product can be from 20 bp in length to one or several kbp, preferably from 50 bp to 1000 bp, more preferably from 100 bp to 600 bp.

In one embodiment, the set of primers comprises a primer (e.g., a forward primer) specific to a portion of the partial intron 3 located within 1000 bp upstream of the breakpoint, preferably within 500 bp upstream of the breakpoint, and more preferably within 200 bp upstream of the breakpoint; and a primer (e.g., a reverse primer) specific to a portion of the Exon2/intron2 region of the duplicated region located within 1000 bp downstream of the breakpoint, preferably with 500 bp downstream of the breakpoint, and more preferably within 200 bp downstream of the breakpoint.

The primer can, for example, be about 18 to about 30 nucleotides, or about 20 to about 50 nucleotides, in length. For example the primer may be from 15, 16, 17, 18, 19 or 20 nucleotides to 22, 25, 28, 30, 35 or 50 nucleotides in length.

In one embodiment, the set of primers includes:
a forward primer comprising, or consisting of, a sequence selecting from the group consisting of:

ACGTGTTGAGGGCATGACCTC (SEQ ID NO: 3)

CTCATCTGGCACAACTCAGCG (SEQ ID NO: 20)

GGCTGACATCATCAGTGACCAAGA (SEQ ID NO: 22)

and
a sequence having at least 90 or 95% identity with one sequence of SEQ ID NOs: 3, 20 and 22;
and/or
a reverse primer comprising, or consisting of, a sequence selecting from the group consisting of:

GCCTGGATTCCTTGTGATACACG (SEQ ID NO: 4)

TTCTTAGCATTTCACACAAATGCATG (SEQ ID NO: 17)

GATCACCTGAACCCAGTGAGGT (SEQ ID NO: 19)

and
a sequence having at least 90 or 95% identity with one sequence of SEQ ID NOs: 4, 19 and 19.

In a particular embodiment, the set of primers includes:
a forward primer consisting of a sequence selecting from the group consisting of SEQ ID NO: 3, SEQ ID NO: 20 and SEQ ID NO: 22 and a sequence having at least 90 or 95% identity with one sequence of SEQ ID NOs: 3, 20 and 22; and/or
a reverse primer consisting of a sequence selecting from the group consisting of: SEQ ID NO: 4, SEQ ID NO: 17 and SEQ ID NO: 19 and a sequence having at least 90 or 95% identity with one sequence of SEQ ID NOs: 4, 17 and 19.

In a specific embodiment, the set of primers includes:
a forward primer comprising, or consisting of, a sequence of SEQ ID NO: 3;
and/or
a reverse primer comprising, or consisting of, a sequence of SEQ ID NO: 4.

In a more specific embodiment, the set of primers includes:
a forward primer consisting of a sequence of SEQ ID NO: 3;
and/or
a reverse primer consisting of a sequence of SEQ ID NO: 4.

In a preferred embodiment, the set of primers includes:
a forward primer consisting of a sequence of SEQ ID NO: 3; and
a reverse primer consisting of a sequence of SEQ ID NO: 4.

In addition, the method may further comprise amplification of a control or reference gene, in particular in order to have a positive control for the amplification reaction. The control or reference gene can be for instance GADPH, ACTB or RASSF1A. Accordingly, step a) may further comprise contacting the DNA sample with a set of primers targeting the control or reference gene. For instance, a pair of primers targeting the GAPDH gene is disclosed in SEQ ID NOs: 7 and 8 and a pair of primers targeting the ACTB gene is disclosed in SEQ ID NOs: 40 and 41.

The method may also further comprise the detection of one or several exons of RHD gene or the detection of one or several mutations or SNPs of interest of the RHD gene. Accordingly, step a) may further comprise contacting the DNA sample with a set of primers targeting one or several exons of RHD gene or targeting one or several mutations or SNPs of interest of the RHD gene. Preferably, at least one of exon 4, exon 5, exon 7, or exon 10 is further detected by amplification. In some embodiments, at least two exons of the RHD gene are detected by amplification. In other embodiments, at least three exons of the RHD gene are detected by amplification. Detection of all possible combinations of each of the preferred exons are contemplated by the methods of the invention. For example, detection of exons 4 and 5; exons 4 and 7; exons 4 and 10; exons 5 and 7; exons 5 and 10; or exons 7 and 10 may be used. Similarly, detection of exons 4, 5, and 7; exons 4, 5, and 10; exons 5, 7, and 10, or exons 4, 7, and 10 may be used. In another embodiment, exons 4, 5, 7, and 10 are detected. The person skilled in the art can easily design appropriate primers. For instance, such primers are disclosed in WO2010/009440 or WO2015/001056 (hereby incorporated herein by reference in their entirety).

In particular, the method further comprises the detection of exon 5 and/or exon 10 of the RHD gene, preferably of exon 5 and exon 10. Indeed, detection of the presence of exons 5 and 10 would be indicative of a Rhesus D+; detection of the presence of exon 10 but not exon 5 would be indicative of a Rhesus D+ but partial; and the absence of exons a Rhesus D−. In a context of a Rhesus D+(detected presence of exons 5 and 10), the present invention, by detection of the presence of exon 3 duplication, could allow the identification of weak D phenotype.

Preferably, the detection is carried out by an amplification step followed by a step of detecting the amplification product. Accordingly, step a) may further comprise contacting the DNA sample with a set of primers targeting the exon 5 and/or exon 10, preferably a set of primers targeting the exon 5 and a set of primers targeting the exon 10. For instance, a pair of primers targeting exon 5 is disclosed in SEQ ID NOs: 1 and 2. Similarly, a pair of primers targeting exon 10 is disclosed in SEQ ID NOs: 5 and 6. Other suitable pair of primers can be designed and used.

In a preferred embodiment, the amplification step is carried out by a PCR reaction, in particular in a multiplex PCR reaction.

In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. The cycle may or may not be repeated. In certain embodiments, a cycle of amplification comprises a multiplicity of amplification cycles, for example, but not limited to 20 cycles, 25 cycles, 30 cycles, 35 cycles, 40 cycles, 45 cycles or more than 45 cycles of amplification.

In certain embodiments, an amplification reaction comprises multiplex amplification, in which a multiplicity of different target nucleic acids and/or a multiplicity of different amplification product species are simultaneously amplified using a multiplicity of different primer sets.

In one embodiment, the amplification steps of the control or reference gene and/or of one or several exons of the RHD gene are carried out concurrently with the amplification step of the duplication of exon 3 of the RHD gene, preferably by a multiplex amplification. In an alternative embodiment, the amplification steps of the control or reference gene and/or of one or several exons of the RHD gene are carried out separately from the amplification step of the duplication of exon 3 of the RHD gene, preferably by a multiplex amplification, in particular in distinct reaction vessels.

In a specific embodiment, the method may comprise a) contacting a first set of primers specific to the duplication of exon 3 of the RHD gene, a second set of primers specific to exon 5 of the RHD gene and a third set of primers specific to exon 10 of the RHD gene with the DNA sample and an amplification reaction mixture in conditions suitable for amplification; and b) detecting an amplification product of each set of primers. In particular, the detection of the presence of amplification products by the first, second and third set of primers is indicative of the presence of a weak D phenotype; the detection of the presence of amplification products by the second and third sets of primers and the absence of an amplification product by the first set of primers is indicative of the presence of a Rhesus D+ phenotype; the detection of the amplification product by the third set of primers and the absence of amplification products by the first and second sets of primers is indicative of the presence of a Rhesus D− phenotype; and/or the absence of amplification products by the first, second and third sets of primers is indicative of the presence of a Rhesus D− phenotype.

Exemplary methods for polymerizing and/or amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for polymerizing and/or amplifying and detecting nucleic acids suitable for use as described herein are commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety).

In a particular embodiment, the amplification reaction mixture comprises a heat-stable DNA polymerase and an appropriate buffer (typically provided with the DNA polymerase), a set of amplification primers and dNTPs. Preferably the DNA polymerase is a high-fidelity DNA polymerase, i.e. with an error rate less than $10^{-5}$, more preferably less than $10^{-6}$. Examples of suitable available DNA polymerases include, but are not limited to, *Pyrococcus furiosus* (Pfu) DNA polymerase (Stratagene), Phusion™ DNA Polymerase (New England Biolabs), Platinum® Taq DNA Polymerase High Fidelity (Life Technologies), PfuUltra™ (Stratagene), or MyFi™ DNA polymerase (Bioline).

The amplification products can be detected by any suitable method well-known by the person skilled in the art. For instance, the amplification products can be detected by an electrophoresis including gel electrophoresis and capillary electrophoresis, mass spectrometry, hybridization with a probe specific to the amplification products, including microarray hybridization or solid support hybridization, and sequencing. In one preferred embodiment, the amplification products are detected by an electrophoresis including gel electrophoresis.

Several methods are now available to the person skilled in the art for carrying out amplification and detecting amplification products.

For instance, TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system suitable for use as described herein utilizes double-stranded probes in displacement hybridization methods (see, e.g., Morrison et al. Anal. Biochem., 18:231-244 (1989); and/or Li, et al. Nucleic Acids Res., 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for polymerizing and/or amplifying and detecting target nucleic acids suitable for use as described herein involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher moiety that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA<®>), a single step isothermal process for polymerizing and/or amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpions™ system is another exemplary assay format that may be used in the methods described herein. Scorpions™ primers are bi-functional molecules in which a primer is covalently linked to the probe, along with a detectable label (e.g., a fluorophore) and a non-detectable quencher moiety that quenches the fluorescence of the detectable label. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexaethylene glycol (HEG) monomer (Whitcombe, et al. Nat. Biotech. 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpions™ system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for such labeled probes are known in the art and would be suitable for use in the methods described herein.

In specific embodiment, the method for amplifying and detecting can be selected from quantitative multiplex PCT of short fluorescent fragments (QMPSF); Multiplex Ligation-dependent Probe Amplification (MLPA) and PCR in Real Time.

In one embodiment, the present invention relates to a probe suitable for detecting a duplication of exon in the RHD gene. Accordingly, the present invention relates to a probe or an oligonucleotide specifically hybridizing a portion of the RHD gene specific to the duplication of exon 3 of the RHD gene, more particularly a portion comprising at least 5, 6, 7, 8, 9 or 10 nucleotides upstream and downstream of the breakpoint of SEQ ID NO: 31, a sequence having at least 90, 95 or 99% of identity with SEQ ID NO: 31 or a complementary sequence thereof.

Figure 5:
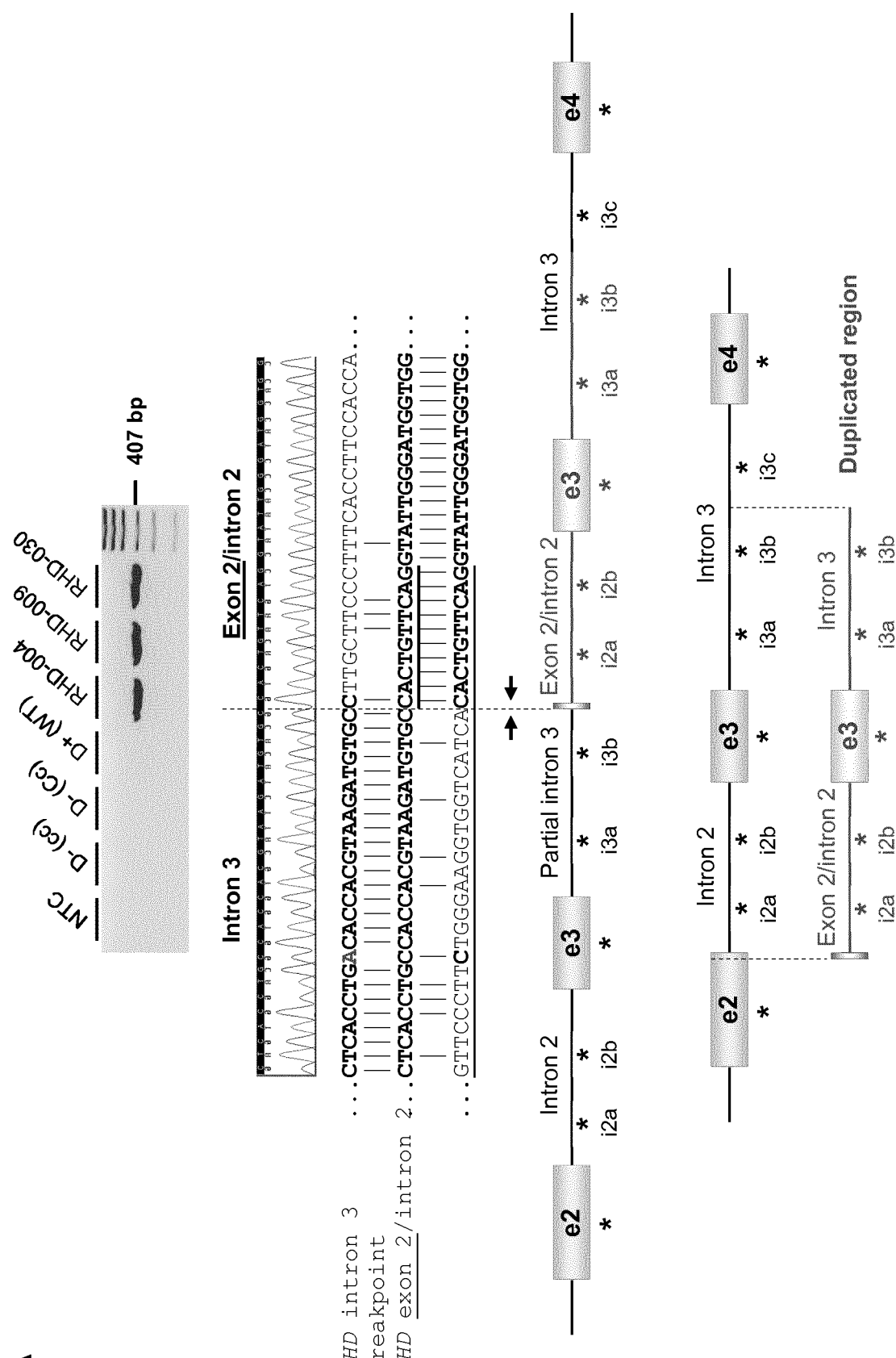
FIG. 5. The novel, Indian weak D allele involves duplication of a ~12-kb fragment inserted within RHD intron 3. (A) A unique, 407-bp PCR product corresponding to a specific breakpoint was identified and sequenced in exon 3 duplication samples (RHD-004, RHD-009, and RHD-030). (B) Schematic representations of the genomic RHD locus ranging from exon 2 to exon 4 (top panel) and the ~12-kb duplicated region (in red), as characterized by QMPSF and sequencing (bottom panel). NTC: no template control; D− (cc): homozygous whole RHD gene deletion control sample (Rh C/c, E/e phenotype: ccee); D− (Cc): homozygous whole RHD gene deletion control sample (Ccee); D+(WT): hemizygous wild-type RHD control sample (Ccee); bp: base pairs. Exon 2 sequence is underlined; arrows: RHD_i3ex3dup_F/RHD_i2ex3dup_R PCR primers; *: QMPSF markers.

The probe is a nucleic acid including the breakpoint between intron 3 and exon 2 as shown in FIG. 5 (SEQ ID NO: 31 between position 26 and 27). Preferably, the probe comprise at least 5, 6, 7, 8, 9, 10, 15, 20 or 25 nucleotides upstream and downstream of the breakpoint of SEQ ID NO: 31, a sequence having at least 90, 95 or 99% of identity with SEQ ID NO: 31 or a complementary sequence thereof.

The probe can be labeled. In particular, the probe may comprise a fluorescent molecule, e.g., at its 5' and 3'. Optionally, the probe may further comprise a quencher molecule, in particular suitable for quenching the fluorescent molecule.

In one embodiment, the means suitable for detecting a duplication of exon in the RHD gene combines a probe and a set of primers.

The present invention relates to an isolated, synthetic or recombinant nucleic acid comprising or consisting of a sequence comprising at least 10, 11, 12, 13, 14, 15, 20 or 25 nucleotides upstream and downstream of the breakpoint of SEQ ID NO: 31, or a sequence having at least 80, 85, 90 or 95% of identity therewith or a complementary sequence thereto. It also relates to an isolated, synthetic or recombinant nucleic acid comprising or consisting of a sequence of SEQ ID NO: 31 or a sequence having at least 80, 85, 90 or 95% of identity therewith or a complementary sequence thereto. In one embodiment, the nucleic acid may comprise or consist of a sequence of SEQ ID NO: 35. The nucleic acid may be at least 20, 25, 30, 40, 50, 75 or 100 bp in length. The nucleic acid may be for instance between 30 and 1000 bp in length, preferably between 50 and 500 bp. Said nucleic acid can be a probe or an amplification product. Said nucleic acid may comprise a label. The label can be a fluorescent label, a sequence tag (heterologous to the RHD gene) and the like. Said nucleic acid may comprise a fluorescent molecule and a quencher, in particular suitable for quenching the fluorescent molecule.

The present invention relates to an isolated or recombinant nucleic acid carrying a duplication of exon 3 of the RHD gene. In particular, it relates to a nucleic acid encoding a rhesus D antigen and carrying a duplication of exon 3 of the RHD gene. In one embodiment, the nucleic acid comprises the duplicated region of SEQ ID NO: 34 or a sequence having at least 90, 95, 98 or 99% of identity with SEQ ID NO: 34.

The present invention also relates to a kit. The kit is suitable for detecting the presence of a duplication of exon 3 of the RHD gene in a DNA sample, for determining RHD genotype or for detecting a weak D phenotype, wherein the kit comprises means suitable for specifically detecting a duplication of exon 3 of the RHD gene in a DNA sample. Preferably, the means can be a probe or a set of primers specific to the duplication of exon 3 of the RHD gene in the DNA sample or a combination thereof.

The kit may comprise any primer, set of primers or probe as disclosed above.

In a specific embodiment, the kit may comprise
a forward primer comprising, or consisting of, a sequence selecting from the group consisting of:

```
                                        (SEQ ID NO: 3)
ACGTGTTGAGGGCATGACCTC (SEQ ID NO: 20)
CTCATCTGGCACAACTCAGCG
and (SEQ ID NO: 22)
GGCTGACATCATCAGTGACCAAGA
```
and
a reverse primer comprising, or consisting of, a sequence selecting from the group consisting of:

```
                                        (SEQ ID NO: 4)
GCCTGGATTCCTTGTGATACACG (SEQ ID NO: 17)
TTCTTAGCATTTCACACAAATGCATG (SEQ ID NO: 19)
GATCACCTGAACCCAGTGAGGT.
```

More specifically, the kit may comprise:
a forward primer comprising, or consisting of, a sequence

```
                                        (SEQ ID NO: 3)
ACGTGTTGAGGGCATGACCTC;
```
and
a reverse primer comprising, or consisting of, a sequence

```
                                        (SEQ ID NO: 4)
GCCTGGATTCCTTGTGATACACG.
```

The kit may further comprise one or several elements selected in the group consisting of:
- a set of primer or a probe specific to exon 5 of the RHD gene;
- a set of primer or a probe specific to exon 10 of the RHD gene; and
- an amplification reaction mixture.

In a specific and preferred embodiment, the kit comprises the following primers:
a primer comprising, or consisting of, a sequence

```
                                        (SEQ ID NO: 3)
ACGTGTTGAGGGCATGACCTC;
```
a primer comprising, or consisting of, a sequence

```
                                        (SEQ ID NO: 4)
GCCTGGATTCCTTGTGATACACG;
```
a primer comprising, or consisting of, a sequence

```
                                        (SEQ ID NO: 1)
ATACCTTTGAATTAAGCACTTCACAGAG;
```
a primer comprising, or consisting of, a sequence

```
                                        (SEQ ID NO: 2)
ACTGTGACCACCCAGCATTCTA;
```
a primer comprising, or consisting of, a sequence

```
                                        (SEQ ID NO: 5)
AGGCTGTTTCAAGAGATCAAGCCA;
```
and
a primer comprising, or consisting of, a sequence

```
                                        (SEQ ID NO: 6)
GATGTTGTTATGTGGTACATGGCTG.
```

The kit may also comprise a leaflet.

The present invention further relates to the use of a kit for detecting the presence of a duplication of exon 3 of the RHD gene in a DNA sample, for determining RHD genotype or for detecting a weak D phenotype.

EXAMPLES

Example 1: Novel "RHD Duplication Exon 3" Allele

Although variability of Rh expression has been documented in the large Indian population, genetic studies have not been carried out so far. Then the inventors sought to characterize the molecular bases of weak D expression in Indians. To this aim, a subset of samples presenting with a weak D phenotype by serological analyses (n=223) was genotyped in the RHD gene by conventional molecular approaches. While referenced and novel single nucleotide variations were found, a novel ~12-kilobase duplication event, including exon 3, was identified predominantly in weak D samples (130/223, 58.3%) and characterized at the molecular level. Further functional analyses showed that this genetic variation results in the expression of several transcripts, including a wild-type product. These results suggest that this allele quantitatively affects the expression of the normal transcript, and then subsequently the expression of the normal RhD protein, finally resulting in a weak D phenotype. Overall the present data describe a novel, major weak D allele in the Indian population that may be easily identified in routine by implementing an "Indian-specific, RHD genotyping assay" designed by the inventors.

A Novel Duplication is the Predominant Weak D Allele in Indians

As the inventors initially had no clue about the molecular variants in 223 samples, they first tested the Tm-shift screening assay for genotyping carrying weak D type 1 and/or weak D type 3 alleles in a subset of C+ samples (n=36) (Fichou et al., 2013, Transfusion, 53, 1821-1828). No variant allele was identified by this method. All ten RHD exons were then directly sequenced in these samples. To the inventors surprise, single nucleotide variations were found in only 3/36 (8.3%) samples, suggesting that this mutational mechanism is not so common in the Indian population.

The inventors then thought to genotype the samples by another method that has proven its potency in such a context, i.e. RHD QMPSF, which is more specifically dedicated to the identification of exon CNVs (Fichou et al, 2013, Transfusion, 53(11 suppl 2), 2974-2982). A common profile consisting of the RHD gene at the hemizygous state with an additional exon 3 was found in 26/36 samples by RHD QMPSF (FIG. 1). As a hybrid RHCE-D(3)-CE hybrid gene could be suspected from this result at the CE locus, samples were subsequently analyzed by RHCE QMPSF. This latter method indicated a wild-type pattern with two RHCE copies in all samples. These results suggest that 1) 26 samples of the subset share a common novel allele including two copies of RHD exon 3, and 2) RHD QMPSF is currently the most efficient genotyping method available in our laboratory for RHD screening in this population.

All samples were then primarily genotyped by this latter method. Overall 130/223 (58.3%) samples, including three homozygous samples, showed the specific exon 3 duplication profile, suggesting that this allele is the most common genetic defect resulting in the expression of a weak D phenotype in the Indian population. As all hemizygous and homozygous samples are Ccee and CCee, respectively, the inventors conclude that exon 3 duplication allele is in cis with a RHCE*Ce (or RHCE*02) allele.

Figure 2:
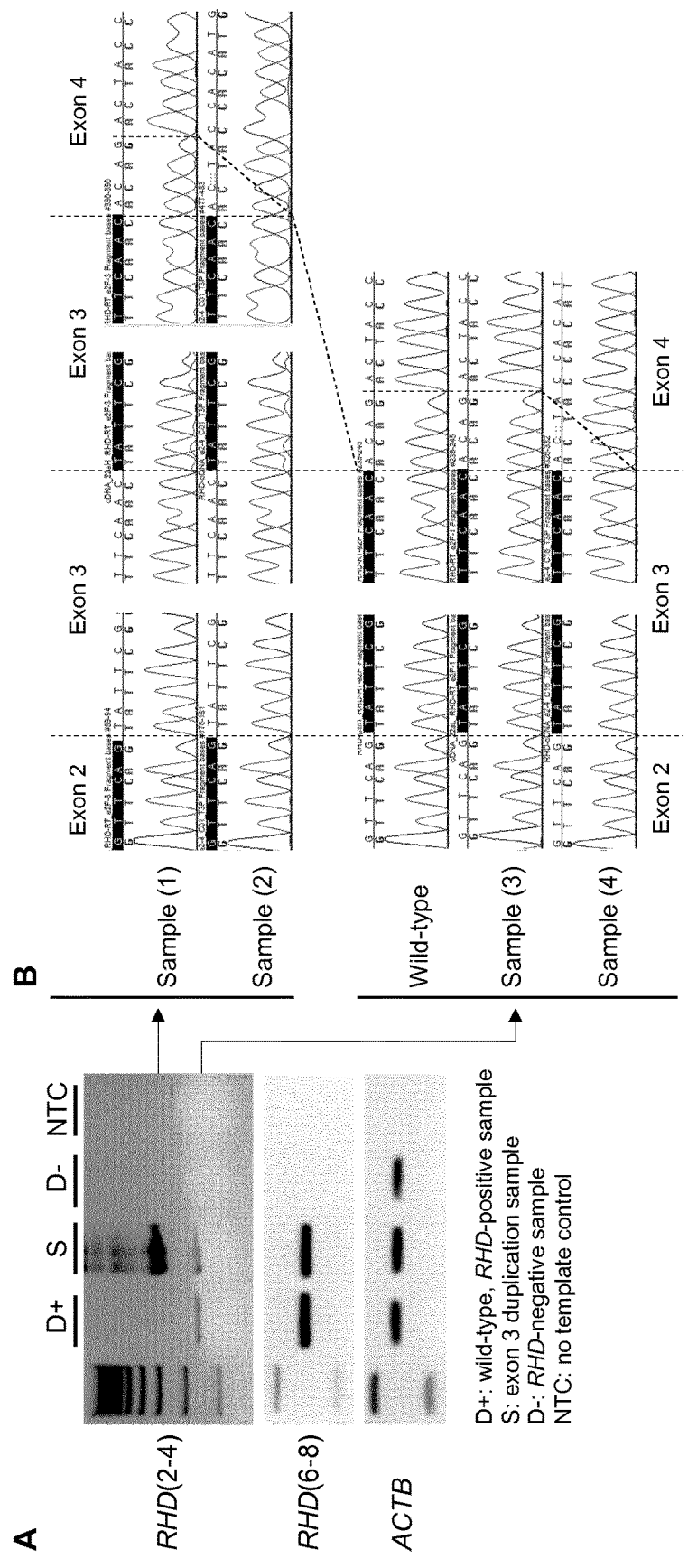
FIG. 2. The novel variant RHD allele including duplication of exon 3 impairs cellular splicing. (A) RT-PCR products were generated by targeting RHD exons 2 to 4 (RHD (2-4)), RHD exons 6 to 8 (RHD(6-8)), and ACTB. Products were loaded on a 2% agarose gel. (B) RT-PCR products from RHD(2-4) amplification were extracted from the gel, subcloned into a commercial vector and sequenced. Four products were found from an exon 3 duplication sample: (1) exon 2-exon 3-exon 3-exon 4; (2) exon 2-exon 3-exon 3-exon 4 deleted from the first four base pairs; (3) exon 2-exon 3-exon 4, identical to what observed in a wild-type sample; and (4) exon 2-exon 3-exon 4 deleted from the first four base pairs.

Exon 3 Duplication is a Splicing Variant that Affects Quantitatively the Expression of D Antigen To get insights into the mechanism involved in the expression of a weak D phenotype due to exon 3 duplication, the inventors sought to characterize the functional consequences of this allele. Total RNA of wild-type, RHD-negative and exon 3 duplication samples were extracted and analyzed by RT-PCR with primers targeting exons 2 and 4 specifically. Interestingly, while a single product composed by exons 2, 3, and 4 was found in the wild-type sample, several products were observed in the variant sample (FIG. 2). Subsequent sequencing revealed different combinations, including more importantly one wild-type product, suggesting that a full RhD protein may be biosynthesized; and another major product composed successively by exons 2 and 3; an additional, full-length exon 3; and finally exon 4. This latter result provides important information about both the genomic rearrangement and the functional mechanism involved in the expression of a weak D phenotype. Indeed it respectively suggests that 1) an additional exon 3 is located between exons 2 and 4 in the same orientation; and 2) although splicing is severely altered and production of wild-type transcript decreases, a wild-type RhD protein may be generated at a low level in agreement with the expression of a weak D phenotype.

Figure 3:
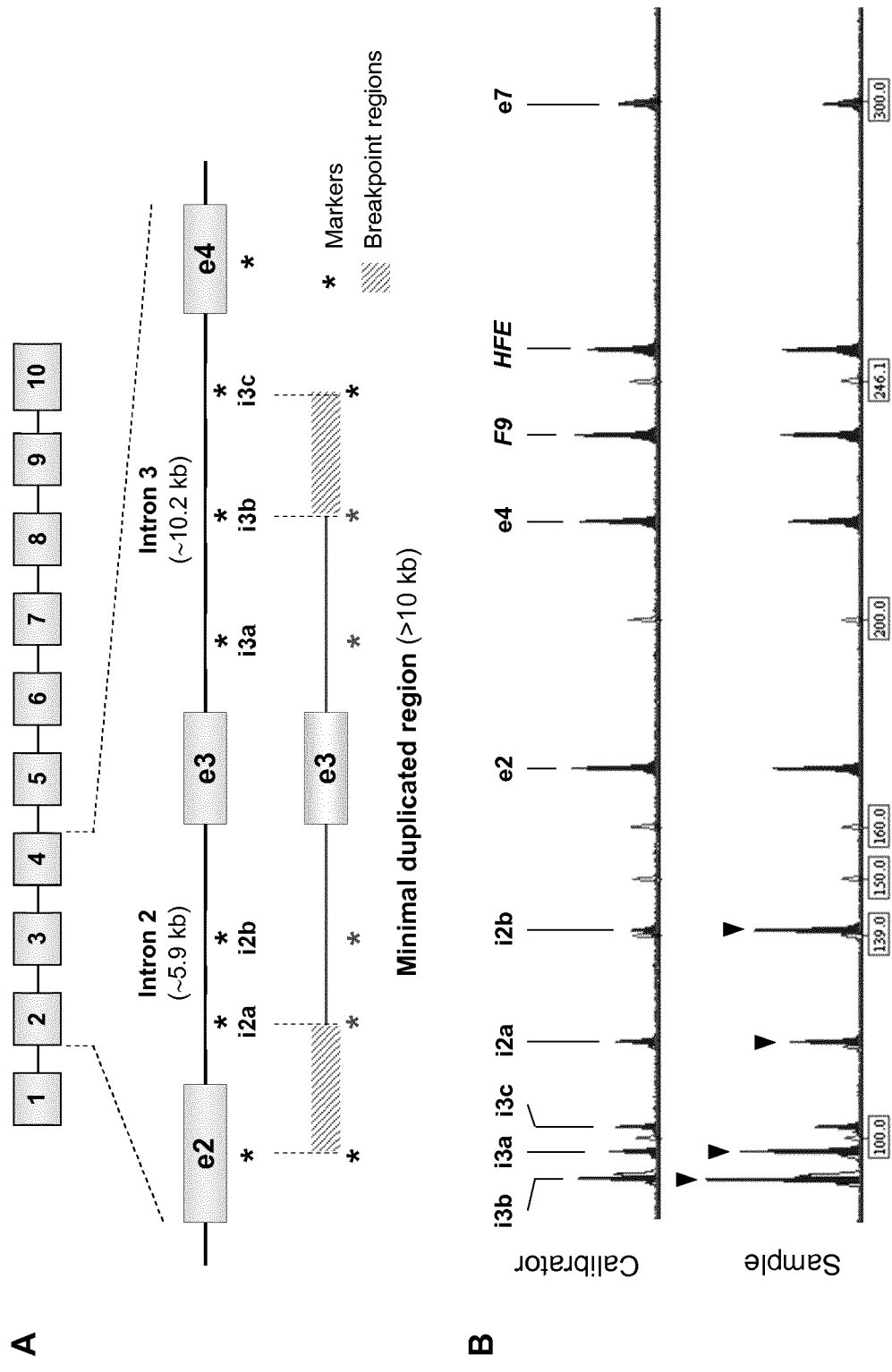
FIG. 3. Customized QMPSF identified a >10-kb duplicated region in weak D individuals. (A) A novel QMPSF assay was designed by positioning additional markers (*) in introns 2 (i2a, and i2b) and 3 (i3a, i3b, and i3c). (B) Typical QMPSF profiles obtained with a hemizygous, wild-type RHD calibrator (Rh C/c, E/e phenotype: Ccee) (top panel); and a hemizygous (exon 3 duplication) sample (Ccee). Calibrator: hemizygous, wild-type RHD control sample; sample: weak D, hemizygous exon 3 duplication sample. Arrowheads indicate copy number variation of markers; e2, e4, e7: RHD exons 2, 4 and 7, respectively.
Figure 4:
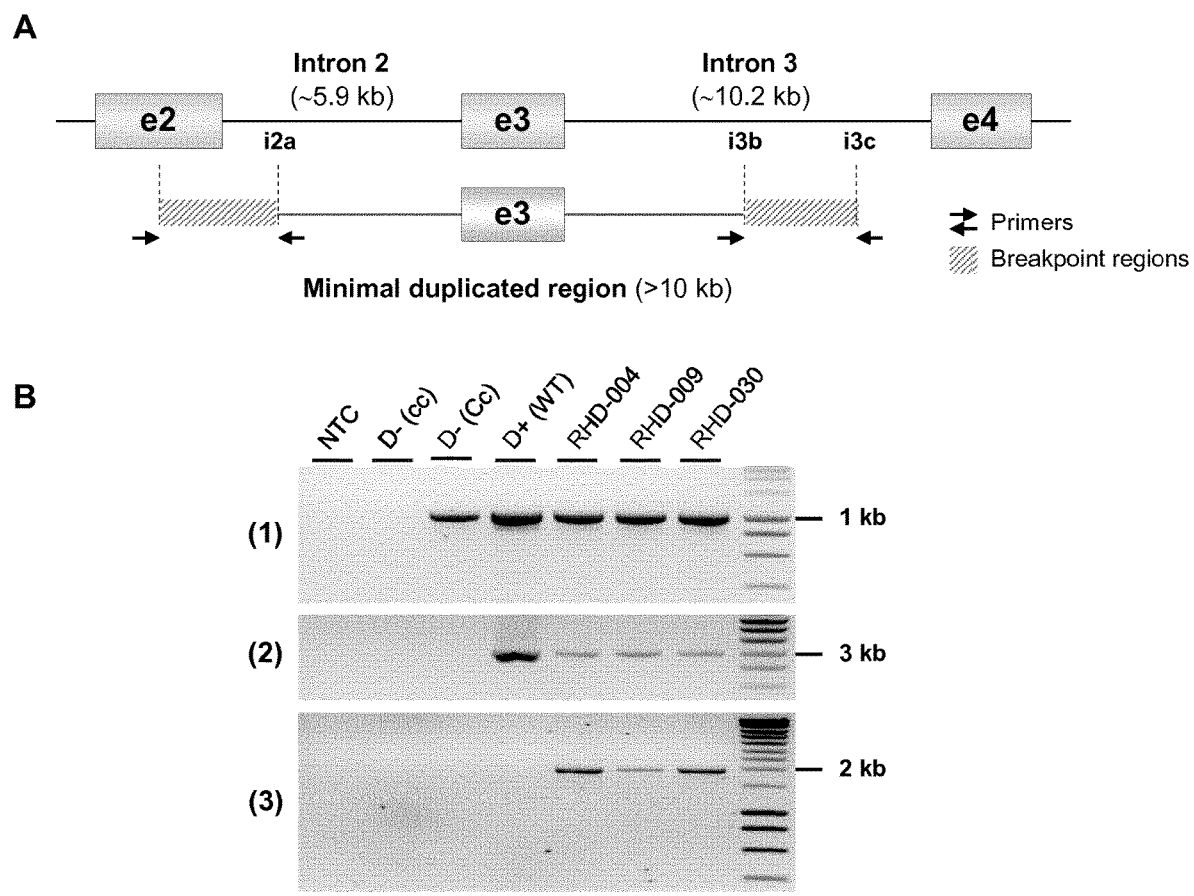
FIG. 4. The novel, Indian weak D allele involves duplication of a ~12-kb fragment inserted within RHD intron 3. (A) Schematic representation of primer positions for PCR amplifications to characterize the duplicated region. (B) Three PCR primer sets (supplemental Table SI) were used to amplify specific markers: (1) PCR amplification with RHD_e2 (forward)/RHD_i2a (reverse) primers is specific to C-positive samples and is ~1 kb in length in all positive lanes (top gel); (2) PCR amplification with RHD_i3b (forward)/RHD_i3c (reverse) primers is specific to D-positive samples, including exon 3 duplication samples and is ~3 kb in length in all positive lanes; and (3) PCR amplification with RHD_i3b (forward)/RHD_i2a (reverse) primers is only specific to exon 3 duplication samples and is ~2 kb in length in all positive lanes. NTC: no template control D− (cc): homozygous whole RHD gene deletion control sample (Rh C/c, E/e phenotype: ccee); D− (Cc): homozygous whole RHD gene deletion control sample (Ccee); D+ (WT): hemizygous wild-type RHD control sample (Ccee); bp: base pairs; RHD-004, RHD-009, and RHD-030: exon 3 duplication samples (Ccee). e2, e3, and e4: RHD exons 2, 3, and 4, respectively; kb: kilobases.
Figure 6:
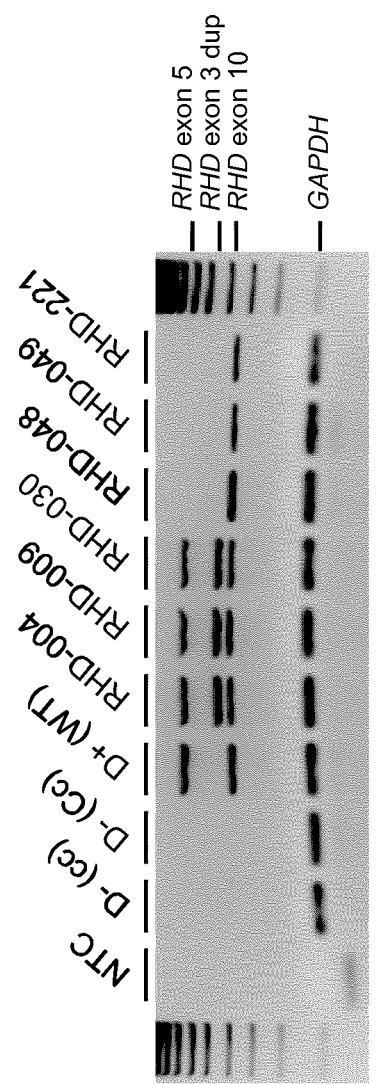
FIG. 6. Indian-specific, multiplex PCR RHD genotyping assay for routine analysis. Typical 1.5% agarose gel profile obtained by multiplex PCR amplification. NTC: no template control; D− (cc): homozygous whole RHD gene deletion control sample (Rh C/c, E/e phenotype: ccee); D− (Cc): homozygous whole RHD gene deletion control sample (Ccee); D+(WT): hemizygous wild-type RHD control sample (Ccee); RHD-004, RHD-009, and RHD-030: exon 3 duplication samples; RHD-048, RHD-049 and RHD-221: other "partial" D alleles. cc and Cc: phenotype RhCc. GAPDH: 97 base pairs (bp); RHD exon 10: 344 bp; RHD exon 3 dup: 407 bp; RHD exon 5: 605 bp.

To characterize the duplication event at the genomic level, the inventors designed a novel QMPSF assay to quantify several markers from exon 2 to exon 4 in 30 samples characterized as carrying an additional exon 3 by QMPSF (FIG. 3). A common genomic region spanning >10-kb was found to be duplicated. To identify the breakpoint(s), a series of PCR amplifications using QMPSF primers was carried out. While normal PCR amplifications were observed in intron 2 and intron 3, an additional, ~2-kb PCR product was shown to be specifically amplified in exon 3 duplication samples with forward and reverse primers located within intron 3 and intron 2, respectively (FIG. 4). Other PCR primers were then designed to amplify a specific marker with minimal length. Finally a 407-bp fragment could be amplified and strictly showed the same sequence in 90 samples, including the 3'-end region of exon 2 (FIG. 5), suggesting a single mutational event. Overall the duplicated region was shown to be ~12 kb in length, ranging from exon 2 to intron 3, and is inserted within intron 3 (FIG. 6).

Example 2: Genotyping Assay

Indian-specific, RHD gene variant genotyping assay is based on the multiplex Polymerase Chain Reaction (PCR) principle. Several PCR primers are mixed together for the specific amplification of four human genome targets. Targets are: 1) GAPDH; 2) RHD exon 10; 3) RHD exon 5; and 4) a specific RHD gene region of a novel weak D allele ("RHD duplication exon 3") specifically identified in the Indian population. This primer pool is combined with a commercial PCR master mix, including thermostable DNA polymerase and genomic DNA, for PCR amplification of targets in a thermal cycler in standard conditions. PCR products are loaded onto an agarose gel for visualization and sizing. Samples exhibiting a specific "RHD duplication exon 3" band carry the novel variant D allele and may be considered as "wild-type" (i.e. D+).

This genotyping assay was designed to simplify RHD genotyping in the Indian population. After characterizing the novel "RHD duplication exon 3" allele, an assay was designed for the rapid screening of this allele. This test is based on the Polymerase Chain Reaction (PCR) principle, which may be easily implemented in a molecular biology laboratory.

Four targets were selected for the test:
1) GAPDH gene (amplification positive control);
2) RHD exon 10 (positive when RHD is present);
3) RHD exon 5 (positive with wild-type RHD allele; negative with many RHD variant alleles of clinical interest);
4) Specific domain within a novel weak D allele ("RHD duplication exon 3") specifically identified in the Indian population.

Several experimental conditions were tested with different primer concentrations. Finally, a primer pool (concentration 2x) was prepared (Table 1) and tested successfully (FIG. 6). This primer mix is the key-component of the genotyping assay.

TABLE 1

Primer sequences and concentrations in the 2X Primer Pool ($C_{2X}$).

| Target | Size (bp) | SEQ ID NO: | Sequence (5'→3') | $C_{2X}$ (µM) |
|---|---|---|---|---|
| RHD exon 5 | 605 | 1 | ATACCTTTGAATTAAGCACTTCACAGAG | 1.2 |
|  |  | 2 | ACTGTGACCACCCAGCATTCTA | 1.2 |
| RHD exon 3 dup | 407 | 3 | ACGTGTTGAGGGCATGACCTC | 0.4 |
|  |  | 4 | GCCTGGATTCCTTGTGATACACG | 0.4 |
| RHD exon 10 | 344 | 5 | AGGCTGTTTCAAGAGATCAAGCCA | 0.4 |
|  |  | 6 | GATGTTGTTATGTGGTACATGGCTG | 0.4 |

TABLE 1-continued

Primer sequences and concentrations in the 2X Primer Pool ($C_{2X}$).

| Target | Size (bp) | SEQ ID NO: | Primers Sequence (5'→3') | $C_{2X}$ (µM) |
|---|---|---|---|---|
| GAPDH | 97 | 7 | CCCCACACACATGCACTTACC | 0.6 |
|  |  | 8 | CCTAGTCCCAGGGCTTTGATT | 0.6 |

Reagents for carrying out this test are: 1/ Commercial 2×PCR Master Mix, including thermostable DNA polymerase; and 2/ 2× Primer Pool. Reagents are mixed together (V/V). Genomic DNA is added to this mixture prior to PCR amplification. Experimental PCR conditions are typically those described by the PCR Master Mix manufacturer, with a 60° C. annealing temperature as described above.

PCR amplification products are loaded onto an agarose gel for sizing specific bands (FIG. 6) and genotype interpretation by using the interpretation guide (Table 2).

TABLE 2

Interpretation guide of the genotyping assay.

| GAPDH | RHD exon 3 dup | RHD exon 5 | RHD exon 10 | Results |
|---|---|---|---|---|
| − | − | − | − | Re-test |
| + | − | − | − | D negative |
| + | − | − | + | D negative/partial D* |
| + | − | + | + | D positive* |
| + | + | + | + | D positive/weak D |

+: amplification;
−: no amplification. Other combinations are theoretically possible, but have not been tested.
*Other genotyping methods (Sanger sequencing, microarray . . .) may be necessary to characterize genotype accurately.

This assay may be used to genotype samples, and more specifically to identify the most prevalent weak D variant allele in the Indian population (~60% samples presenting with a weak D phenotype) in ~2 hours only after genomic DNA extraction. Test cost is supposed to be less than 1 f (reagent/test). Only thermal cycler and gel electrophoresis unit are necessary to carry out the test. Thus it is a simple, easy-handling cost-effective genotyping assay.

Moreover, this test may be used to identify the molecular basis of D-negative phenotype (i.e. whole RHD gene deletion vs nonfunctional RHD allele), because of the presence of two RHD-specific markers (exon 5 and exon 10).

Materials and Methods

RHD Genotyping and Mapping of the Duplicated Region

RHD gene exons were first amplified by multiplex PCR and sequenced as previously described (Fichou et al., 2013, Transfusion, 53, 1821-1828). Alternatively copy number variations (CNVs) of RHD exons were analyzed by RHD QMPSF for exon quantitation (Fichou et al, 2013b). RHCE QMPSF was carried out when a hybrid RHD-CE-D gene was suspected.

To delineate the duplicated region another QMPSF assay based on universal fluorescent labeling was designed as previously described (Fichou et al, 2013, Transfusion, 53(11 suppl 2), 2974-2982). Additionally to the reference markers in HFE and F9, as well as RHD-specific markers in RHD exons 2, 4, and 7, five other primer sets were designed with PrimerQuest Tool (www.eu.idtdna.com/primerquest/home/index/) with default parameters to amplify markers in introns 2 (n=2; RHD_i2a and RHD_i2b) and 3 (n=3; RHD_i3a, RHD_i3b and RHD_i3c) (Table 3). PCR amplification conditions and analysis methods were as described before (Fichou et al, 2013, Transfusion, 53(11 suppl 2), 2974-2982).

TABLE 3

QMPSF primers and conditions for mapping the duplicated region.

| Marker | Forward primer* (5'→3') | Reverse primer† (5'→3') | Size (bp) | Primer concentration forward/reverse (nM) |
|---|---|---|---|---|
| HFE | U-AGCAGGACCTTGGTCTTTCCTT SEQ ID NO: 10 | H-ACCCTTGCTGTGGTTGTGAT SEQ ID NO: 11 | 254 | 2/200 |
| F9 | U-ACCATGACATTGCCCTTCTGGA SEQ ID NO: 12 | H-AGACATGTGGCTCGGTCAACAA SEQ ID NO: 13 | 238 | 2/200 |
| RHD_e2 | U-CTTGGGCTTCCTCACCTCGAG SEQ ID NO: 14 | H-TGTGATGACCACCTTCCCAGA SEQ ID NO: 15 | 172 | 1/100 |
| RHD_i2a | U-AGCCCCCTAATGCTGCTAGACAAT SEQ ID NO: 16 | H-TTCTTAGCATTTCACACAAATGCATG SEQ ID NO: 17 | 123 | 1/100 |

TABLE 3-continued

QMPSF primers and conditions for mapping the duplicated region.

| Marker | Forward primer* (5'→3') | Reverse primer† (5'→3') | Size (bp) | Primer concentration forward/reverse (nM) |
|---|---|---|---|---|
| RHD_i2b | U-CACTGTG<u>T</u>CC<u>A</u>GCCTAAAACTGT<u>T</u> SEQ ID NO: 18 | H-GATCACCTGAACCCAGTGAGG<u>T</u> SEQ ID NO: 19 | 143 | 4/400 |
| RHD_i3a | U-CTCATCTGGCACAACTCAGC<u>G</u> SEQ ID NO: 20 | H-CCAGATCTATCCCACCCCAA<u>CA</u> SEQ ID NO: 21 | 100 | 2/200 |
| RHD_i3b | U-<u>GG</u>CTGACATCATCAGTGACCAAG<u>A</u> SEQ ID NO: 22 | H-CATCACACTCTCCCTTTCTTGCTG<u>T</u> SEQ ID NO: 23 | 97 | 2/200 |
| RHD_i3c | U-AATCCCCAAGTGTTCTT<u>CC</u>TGAA<u>C</u> SEQ ID NO: 24 | H-TAAGAACTGAAAAGCGGGCTTG<u>T</u> SEQ ID NO: 25 | 107 | 2/200 |
| RHD_e4 | U-ACTACCACATGAAC<u>A</u>TGA<u>T</u>GCAC<u>A</u> SEQ ID NO: 26 | H-CCATTCTGCTCAGCCCAAGTA<u>G</u> SEQ ID NO: 27 | 221 | 3/300 |
| RHD_e7 | U-ACA<u>G</u>CTCC<u>A</u>TCATG<u>GG</u>CT<u>A</u>C<u>AA</u> SEQ ID NO: 28 | H-CCAAGGTAGGGGCTGGACA<u>G</u> SEQ ID NO: 29 | 301 | 4/400 |

RHD-specific nucleotides are underlined; bp: base pairs.
*U refers to as the 20-mer, universal primer sequence 5'-GTCGTAGTCGACGACCGTTA-3' (SEQ ID NO: 9).
†H refers to as the 5'-GTTTCTT-3' nucleotide heptamer.

Indian-Specific RHD Genotyping Assay

PCR primers are mixed at a 2× concentration to amplify four targets: GAPDH, RHD exon 3 duplication marker, RHD exons 5 and 10 markers (Table 1). PCR primer pool was mixed with 1× HotStarTaq Master Mix (Qiagen) and 1 µL genomic DNA (20-100 ng/µL). PCR conditions were: an initial denaturation step at 95° C. for 15 min, followed by 40 cycles of denaturation at 95° C. for 30 sec, annealing at 60° C. for 30 sec, extension at 72° C. for 30 sec; and a final extension step at 72° C. for 10 min. PCR products were loaded on a 1.5% agarose gel for visualization.

Breakpoint Mapping

Breakpoint was PCR-amplified and sequenced with primers RHD_i3ex3dup_F and RHD_i2ex3dup_R in standard conditions.

To characterize the duplicated region, three PCR amplifications were carried out. Primer sets were RHD_e2 (forward)/RHD_i2a (reverse); RHD_i3b (forward)/RHD_i3c (reverse); and RHD_i3b (forward)/RHD_i2a (reverse) (Table 3). Breakpoint was finally PCR-amplified with primers RHD_i3ex3dup_F (5'-ACGTGTTGAGGGCATGACCT<u>C</u>-3' SEQ ID NO: 3) and RHD_i2ex3dup_R (5'-GCCTGGATTCCTTGTGATACAC<u>G</u>-3' SEQ ID NO: 4) (RHD-specific nucleotides are underlined). All PCR amplifications were carried out with HotStarTaq Master Mix Kit (Qiagen, Courtaboeuf, France) in a 10 µL final volume with 1× HotStarTaq Master Mix, 0.4 µM of both forward and reverse primers, and 1 µL genomic DNA solution (20-100 ng/µL) as a template. PCR conditions were: an initial denaturation step at 95° C. for 15 min, followed by 40 cycles of denaturation at 95° C. for 30 sec, annealing at 60° C. for 30 sec, extension at 72° C. for 30 sec; and a final extension step at 72° C. for 10 min.

PCR products were loaded on an agarose gel and treated by USB® ExoSAP-IT® PCR cleanup reagent (Affymetrix, purchased from Ozyme, St-Quentin-en-Yvelines, France) prior to direct sequencing with PCR primers as previously described (Fichou et al, 2013, Transfusion, 53(11 suppl 2), 2974-2982).

Reverse-Transcription (RT)-PCR and Sequencing

Total RNA was extracted from fresh whole blood by using Trizol-based RNA extraction method. Total RNA was reverse-transcribed with Revert Aid First Strand cDNA synthesis kit (Thermo Fisher Scientific Inc., USA) to generate complementary DNA (cDNA) stored at −20° C. until further processing.

One target, i.e. RHD exons 2 to 4 (forward: 5'-CTTGGGCTTCCTCACCTC<u>GAG</u>-3' (SEQ ID NO: 36); reverse: 5'-CGAACACGTAGA<u>T</u>GTGC<u>A</u>TCA<u>T</u>-3' (SEQ ID NO: 37)), one RHD-positive control, i.e. RHD exons 6 to 8 (forward: 5'-GAGCCAAGT<u>A</u>CCTGCCGG<u>G</u>-3' (SEQ ID NO: 38); reverse: 5'-ATCATGCCATTGCCG<u>GCT</u>-3' (SEQ ID NO: 39)) and one reference gene, i.e. ACTB (forward: 5'-TCTCCATGTCGTCCCAGTTG-3' (SEQ ID NO: 40); reverse: 5'-AGTCTTCCCCTCCATCGTTG-3' (SEQ ID NO: 41)) were amplified by PCRs (RHD-specific nucleotides are underlined). PCR amplifications were carried out with HotStarTaq Master Mix Kit (Qiagen, Courtaboeuf, France) in a 10 µL final volume with 1× HotStarTaq Master Mix, 0.4 µM of both forward and reverse primers, and 1 µL cDNA solution as a template. PCR conditions were as describe above.

PCR products were loaded on an agarose gel, gel-purified with QIAquick Gel Extraction Kit (Qiagen), and subcloned into the pCR™ 4-TOPO® Vector by using the TOPO® TA Cloning® Kit for Sequencing (Thermo Fisher Scientific, Courtaboeuf, France) according to the manufacturer's instructions. Cloning products were transformed into One Shot® TOP10 Chemically Competent E. coli (Thermo Fisher Scientific) and directly sequenced by T7 and T3 primers in conditions previously described (Fichou et al, 2013, Transfusion, 53(11 suppl 2), 2974-2982).

The invention claimed is:

1. A method for detecting the presence of a duplication of exon 3 of the RHD gene in a DNA sample comprising:
   contacting a probe or a set of primers specific to the duplication of exon 3 of the RHD gene with the DNA sample, and
   detecting a hybridization of the probe or an amplification product of the set of primers,
   wherein the detection of said hybridization or said amplification product is indicative of the presence of a duplication of exon 3 of the RHD gene in the DNA sample,
   wherein the probe is specific to the duplication of exon 3 of the RHD gene and specifically hybridizes to a portion of the RHD gene specific to the duplication of exon 3 comprising at least 5 nucleotides upstream of the breakpoint in SEQ ID NO: 31 and comprising at least 5 nucleotides downstream of the breakpoint in SEQ ID NO: 31, or the complement thereof; and
   wherein the set of primers specific to the duplication of exon 3 of the RHD gene comprises a forward primer specific to the partial intron 3 located upstream of the breakpoint in SEQ ID NO: 31 and a reverse primer specific to the Exon2/intron2 region of the duplicated region located downstream of the breakpoint in SEQ ID NO: 31.

2. The method according to claim 1, wherein the probe or the amplification product has a sequence comprising at least 5 nucleotides upstream and at least 5 nucleotides downstream of the breakpoint of SEQ ID NO: 31 or the complement thereof, the probe or amplification product having at least 20 nucleotides in length.

3. The method according to claim 1, wherein the method comprises:
   a) contacting a set of primers specific to the duplication of exon 3 of the RHD gene with the DNA sample and an amplification reaction mixture;
   b) producing the amplification product using a primer-dependent DNA amplification reaction; and
   c) detecting the amplification product, the detection of said amplification product being indicative of the presence of a duplication of exon 3 of the RHD gene in the DNA sample.

4. The method according to claim 3, wherein the step b) is a multiplex amplification.

5. The method according to claim 3, wherein the primer-dependent DNA amplification reaction is a PCR reaction.

6. The method according to claim 1, wherein the method further comprises the detection of the presence of one or several exons of the RHD gene.

7. The method according to claim 1, wherein the set of primers comprises:
   a forward primer specific to a sequence of the partial intron 3 located within 1000 bp upstream of the breakpoint in SEQ ID NO: 31; and
   a reverse primer specific to a sequence of the Exon2/intron2 region of the duplicated region located within 1000 bp downstream of the breakpoint in SEQ ID NO: 31.

8. The method according to claim 1, wherein the set of primers includes:
   a forward primer comprising, or consisting of, a sequence selected from the group consisting of:

```
                                         (SEQ ID NO: 3)
   ACGTGTTGAGGGCATGACCTC;

(SEQ ID NO: 20)
   CTCATCTGGCACAACTCAGCG;
   and (SEQ ID NO: 22)
   GGCTGACATCATCAGTGACCAAGA;
```
   and
   a reverse primer comprising, or consisting of, a sequence selected from the group consisting of:

```
                                         (SEQ ID NO: 4)
   GCCTGGATTCCTTGTGATACACG;

(SEQ ID NO: 17)
   TTCTTAGCATTTCACACAAATGCATG;
   and (SEQ ID NO: 19)
   GATCACCTGAACCCAGTGAGGT.
```

9. The method according to claim 8, wherein the set of primers includes:
   a forward primer comprising, or consisting of, a sequence

```
                                         (SEQ ID NO: 3)
   ACGTGTTGAGGGCATGACCTC;
```
   and
   a reverse primer comprising, or consisting of, a sequence

```
                                         (SEQ ID NO: 4)
   GCCTGGATTCCTTGTGATACACG.
```

10. A method for determining RHD genotype or for detecting a weak D phenotype, comprising detecting the presence of a duplication of exon 3 of the RHD gene in a DNA sample according to claim 1, wherein the presence of a duplication of exon 3 of the RHD gene in the DNA sample is indicative of a weak D phenotype.

* * * * *

UNITED STATES PATENT AND TRADEMARK OFFICE
CERTIFICATE OF CORRECTION

PATENT NO. : 11,248,261 B2
APPLICATION NO. : 16/491645
DATED : February 15, 2022
INVENTOR(S) : Yann Fichou and Swati Kulkarni Page 1 of 1

It is certified that error appears in the above-identified patent and that said Letters Patent is hereby corrected as shown below:

In the Specification

Column 22,
Line 12, "than 1 f" should read --than 1 €--.

Signed and Sealed this
Fourth Day of October, 2022

Katherine Kelly Vidal
*Director of the United States Patent and Trademark Office*